(12) United States Patent
Lee et al.

(10) Patent No.: US 9,782,128 B2
(45) Date of Patent: Oct. 10, 2017

(54) WEARABLE DEVICE AND METHOD FOR CONTROLLING THE SAME

(71) Applicant: Samsung Electronics Co., Ltd., Suwon-si (KR)

(72) Inventors: Jea-Hyuck Lee, Anyang-si (KR); Jin-Hong Min, Suwon-si (KR); In-Geol Baek, Icheon-si (KR); Min-Hyoung Lee, Seongnam-si (KR); Jae-Geol Cho, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 14/991,867

(22) Filed: Jan. 8, 2016

(65) Prior Publication Data

US 2016/0199002 A1    Jul. 14, 2016

(30) Foreign Application Priority Data

Jan. 9, 2015  (KR) .................. 10-2015-0003365

(51) Int. Cl.
*A61B 5/00* (2006.01)
*A61B 5/01* (2006.01)
(Continued)

(52) U.S. Cl.
CPC .......... *A61B 5/6844* (2013.01); *A61B 5/0008* (2013.01); *A61B 5/0059* (2013.01);
(Continued)

(58) Field of Classification Search
CPC .... A61B 5/6801; A61B 5/6824; A61B 5/6844
USPC .................................................... 340/539.12
See application file for complete search history.

(56) References Cited

U.S. PATENT DOCUMENTS

| | | |
|---|---|---|
| 6,453,184 B1 | 9/2002 | Hyogo et al. |
| 2007/0276271 A1 | 11/2007 | Chan |

(Continued)

FOREIGN PATENT DOCUMENTS

| | | |
|---|---|---|
| JP | 2008-023341 | 2/2008 |
| KR | 2006-0027590 | 3/2006 |
| KR | 2009-0099147 | 9/2009 |

OTHER PUBLICATIONS

International Search Report mailed Apr. 22, 2016 corresponding to International Patent Application No. PCT/KR2016/000207.

(Continued)

*Primary Examiner* — Kevin Kim
(74) *Attorney, Agent, or Firm* — McAndrews, Held & Malloy, Ltd.

(57) ABSTRACT

Provided are a wearable device and a method for controlling the same. The wearable device may include a distance sensor unit configured to output a first signal for determining a distance between a user and the wearable device and to receive the first signal reflected from the user. The wearable device may also include a biometric sensor unit configured to output a second signal for determining biometric information of the user and to receive the second signal reflected from the user, and a controller configured to determine the distance based on the received first signal and to obtain the biometric information of the user based on a change in an attribute of the received second signal. The controller may control the biometric sensor unit to output the second signal if the determined distance is equal to or less than a reference distance.

26 Claims, 29 Drawing Sheets

(51) Int. Cl.
*A61B 5/024* (2006.01)
*A61B 5/0205* (2006.01)

(52) U.S. Cl.
CPC ............ *A61B 5/01* (2013.01); *A61B 5/02427* (2013.01); *A61B 5/02438* (2013.01); *A61B 5/681* (2013.01); *A61B 5/7246* (2013.01); *A61B 5/742* (2013.01); *A61B 5/002* (2013.01); *A61B 5/02055* (2013.01); *A61B 5/7475* (2013.01); *A61B 2503/10* (2013.01)

(56) References Cited

U.S. PATENT DOCUMENTS

| | | |
|---|---|---|
| 2008/0019218 A1 | 1/2008 | Klopfenstein et al. |
| 2008/0045806 A1 | 2/2008 | Keppler |
| 2008/0216171 A1 | 9/2008 | Sano et al. |
| 2011/0224508 A1 | 9/2011 | Moon |
| 2012/0150047 A1 | 6/2012 | Terumoto et al. |
| 2013/0338460 A1 | 12/2013 | He et al. |
| 2014/0059066 A1 | 2/2014 | Koloskov |
| 2014/0073486 A1 | 3/2014 | Ahmed et al. |
| 2014/0288392 A1* | 9/2014 | Hong ................. A61B 5/02427 600/301 |

OTHER PUBLICATIONS

Written Opinion of the International Searching Authority mailed Apr. 22, 2016 corresponding to International Patent Application No. PCT/KR2016/000207.

* cited by examiner

WEARABLE DEVICE AND METHOD FOR CONTROLLING THE SAME

CROSS-REFERENCE TO RELATED APPLICATION(S)

This application claims the benefit under 35 U.S.C. §119(a) of a Korean patent application filed in the Korean Intellectual Property Office on Jan. 9, 2015 and assigned Serial No. 10-2015-0003365, the entire disclosure of which is incorporated herein by reference.

BACKGROUND

Various embodiments of the present disclosure relate to a wearable device and a method for controlling the same.

With the rapid spread of electronic devices such as smartphones, most of the world has already witnessed one electronic device per person. This means that the electronic devices have become a part of people's daily lives, and in practice, people have recognized that the electronic devices make their lives easier.

The popularization of the electronic devices is leading to the spread of wearable devices performing various functions in association with the electronic devices. The wearable device may include such devices as, for example, a smart watch (Samsung Galaxy Gear™), a smart band, and so forth. The wearable device is generally worn on a user's wrist, and obtains the user's biometric information (e.g., a heart rate) to provide to the user.

The user may move while wearing the wearable device and this may provide an unwanted input to the wearable device with respect to the biometric information. Moreover, the conventional wearable device is configured to obtain the user's biometric information, ignoring, for example, the user's body condition such as, for example, skin temperature. As a result, the user's biometric information may be skewed due to the user's body condition. In addition, the conventional wearable device is configured to simply provide the recently obtained biometric information to the user, failing to intuitively provide various information associated with a user's change history of the biometric information.

The above information is presented as background information only to assist with an understanding of the present disclosure. No determination has been made, and no assertion is made, as to whether any of the above might be applicable as prior art with regard to the present disclosure.

SUMMARY

Various aspects of the present disclosure are to provide a wearable device capable of providing accurate biometric information to a user by considering the effects of the user's motion on the wearable device when obtaining the user's biometric information.

Various aspects of the present disclosure are to provide a method for controlling a wearable device so that accurate biometric information may be provided to a user by considering the effects of the user's motion on the wearable device when obtaining the user's biometric information.

Various aspects of the present disclosure are to provide a wearable device capable of providing accurate biometric information to a user by considering a body condition of the user when obtaining the user's biometric information.

Various aspects of the present disclosure are to provide a method for controlling a wearable device so that accurate biometric information may be provided to a user by considering the user's body condition when obtaining the user's biometric information.

Various aspects of the present disclosure are to provide a wearable device capable of intuitively providing to a user various information associated with a change history of biometric information.

Various aspects of the present disclosure are to provide a method for controlling a wearable device so that various information associated with a change history of biometric information may be intuitively provided to a user.

According to various embodiments of the present disclosure, there is provided a distance sensor unit configured to output a first signal for determining a distance between a user and the wearable device and to receive the first signal reflected from the user when the wearable device is worn by the user. The wearable device may include a biometric sensor unit configured to output a second signal for determining biometric information of the user and to receive the second signal reflected from the user. A controller in the wearable device may be configured to determine the distance based on the reflected first signal and to obtain the biometric information of the user based on changes in an attribute of the reflected second signal, wherein the controller controls the biometric sensor unit to output the second signal if the determined distance is equal to or less than a reference distance.

According to various embodiments of the present disclosure, there is provided a wearable device including a heat providing unit, a temperature sensor unit configured to receive biometric information of a user to sense a skin temperature of the user when the wearable device is worn by the user, and a controller configured to determine the skin temperature of the user based on the biometric information received by the temperature sensor unit and to determine whether the determined skin temperature is less than a reference temperature. The controller may control the heat providing unit to output light for increasing the skin temperature of the user to a skin of the user, if the skin temperature is less than the reference temperature.

According to various embodiments of the present disclosure, there is provided a method for controlling a wearable device, the method including outputting a first signal for determining a distance between a user and the wearable device and receiving the first signal reflected from the user, when the wearable device is worn by the user, determining the distance based on the reflected first signal, outputting a second signal for determining biometric information of the user and receiving the second signal reflected from the user, if the determined distance is equal to or less than a reference distance, and obtaining the biometric information of the user based on a change in an attribute of the reflected second signal.

According to various embodiments of the present disclosure, there is provided a method for controlling a wearable device, the method including receiving biometric information of a user to sense a skin temperature of the user when the wearable device is worn on the user, determining the skin temperature of the user based on the biometric information received by the temperature sensor unit and determining whether the determined skin temperature is equal to or less than a reference temperature, and outputting light for increasing the skin temperature of the user to a skin of the user, if the skin temperature is equal to or less than the reference temperature.

According to various embodiments of the present disclosure, there is provided a wearable device including a first time of flight (ToF) light source configured to output a first signal for determining a distance between a user and the wearable device when the wearable device is worn by the user, a second light source unit comprising a second ToF light source configured to output the first signal and a light source configured to output a second signal for sensing a pulse of the user, a light-receiving unit configured to receive the first signal and the second signal reflected from the user, and a controller configured to determine the distance based on the reflected first signal and to obtain the biometric information of the user based on a change in an attribute of the reflected second signal. The controller controls the light source to output the second signal if the determined distance is equal to or less than a reference distance.

According to various embodiments of the present disclosure, there is provided a wearable device including a controller; a temperature sensor unit configured to sense a skin temperature of a user wearing the wearable device, a first light source unit comprising a first time of flight (ToF) light source configured to output a first signal for increasing the skin temperature, and a second light source unit comprising a second ToF light source configured to output the first signal and a light source configured to output a second signal for obtaining biometric information of the user. The controller controls the ToF light source to output the first signal if the determined skin temperature is equal to or less than a reference temperature.

Other aspects, advantages, and salient features of the disclosure will become apparent to those skilled in the art from the following detailed description, which, taken in conjunction with the annexed drawings, discloses exemplary embodiments of the disclosure.

BRIEF DESCRIPTION OF THE DRAWINGS

Throughout the drawings, it should be noted that like reference numbers are used to depict the same or similar elements, features, and structures, wherein.

Throughout the drawings, like reference numerals will be understood to refer to like parts, components, and structures.

DETAILED DESCRIPTION

Figure 1A:
FIGS. 1A and 1B are exemplary diagrams for describing a wearable device worn by a user according to various embodiments of the present disclosure.

Hereinafter, various embodiments of the present disclosure will be disclosed with reference to the accompanying drawings. However, the present disclosure is not intended to limit the present disclosure to particular embodiments, and it should be construed as including various modifications, equivalents, and/or alternatives according to the embodiments of the present disclosure. In regard to the description of the drawings, like reference numerals refer to like elements.

Although ordinal numbers such as "first," "second," and so forth will be used to describe various components of the present disclosure, those components are not limited by the terms. The terms are used only for distinguishing one component from another component. For example, a first component may be referred to as a second component and, likewise, a second component may be referred to as a first component without departing from the teachings of the disclosure. The term "and/or" used herein includes any and all combinations of one or more of the associated listed items. The term "or" indicates one item or the other. For example, "A or B" indicates just A or just B.

The terminology used herein is for the purpose of describing various embodiments only and is not intended to be limiting on any embodiment. As used herein, the singular forms are intended to include the plural forms, as well, unless the context clearly indicates otherwise. It will be further understood that the terms "comprises", "includes", and/or "has" in this specification specify the presence of a stated feature, number, step, operation, component, element, or a combination thereof but do not preclude the presence or addition of one or more other features, numbers, steps, operations, components, elements, or combinations thereof.

Any term in this disclosure should first be used as defined or explained in context in this disclosure. Any undefined term used herein, including technical and scientific terms, have the same meanings as terms that are generally understood by those skilled in the art unless otherwise indicated. The next step to clarifying a term would be its definition in a technical dictionary related to the field of this disclosure. The next step would be the definition of the term in a general purpose dictionary.

Figure 1B:
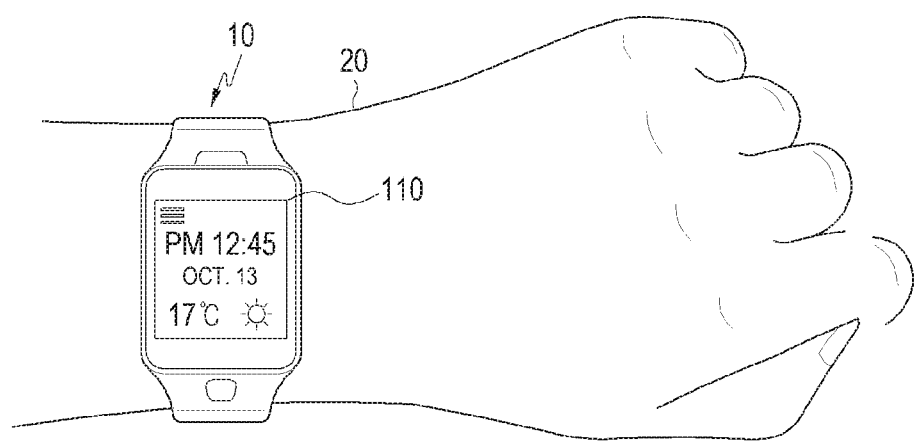

FIGS. 1A and 1B are exemplary diagrams for describing a wearable device worn by a user according to various embodiments of the present disclosure.

Referring to FIGS. 1A and 1B, a wearable device 10 according to various embodiments of the present disclosure may be worn on a wrist of a user 20. Although not shown in FIG. 1A, the wearable device 10 may be worn on another body part (e.g., an ankle) of the user 20. The wearable device 10 according to various embodiments of the present disclosure may be worn by the user 20 to obtain biometric information when the user 20 is involved in an activity such as, for example, jogging or exercising. The wearable device 10 may be able to provide various information associated with the biometric information to the user 20 through a display unit 110.

Figure 2A:
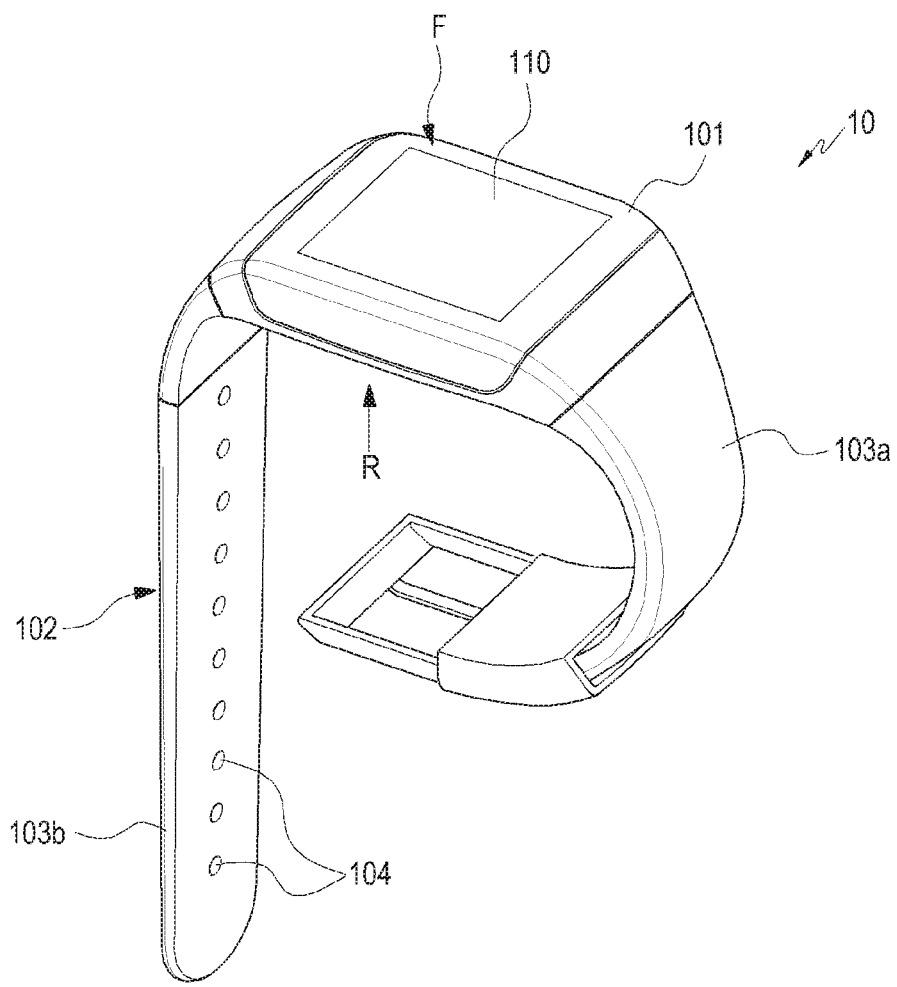
FIGS. 2A through 2C are exemplary diagrams for describing a structure of a wearable device according to various embodiments of the present disclosure.
Figure 2B:
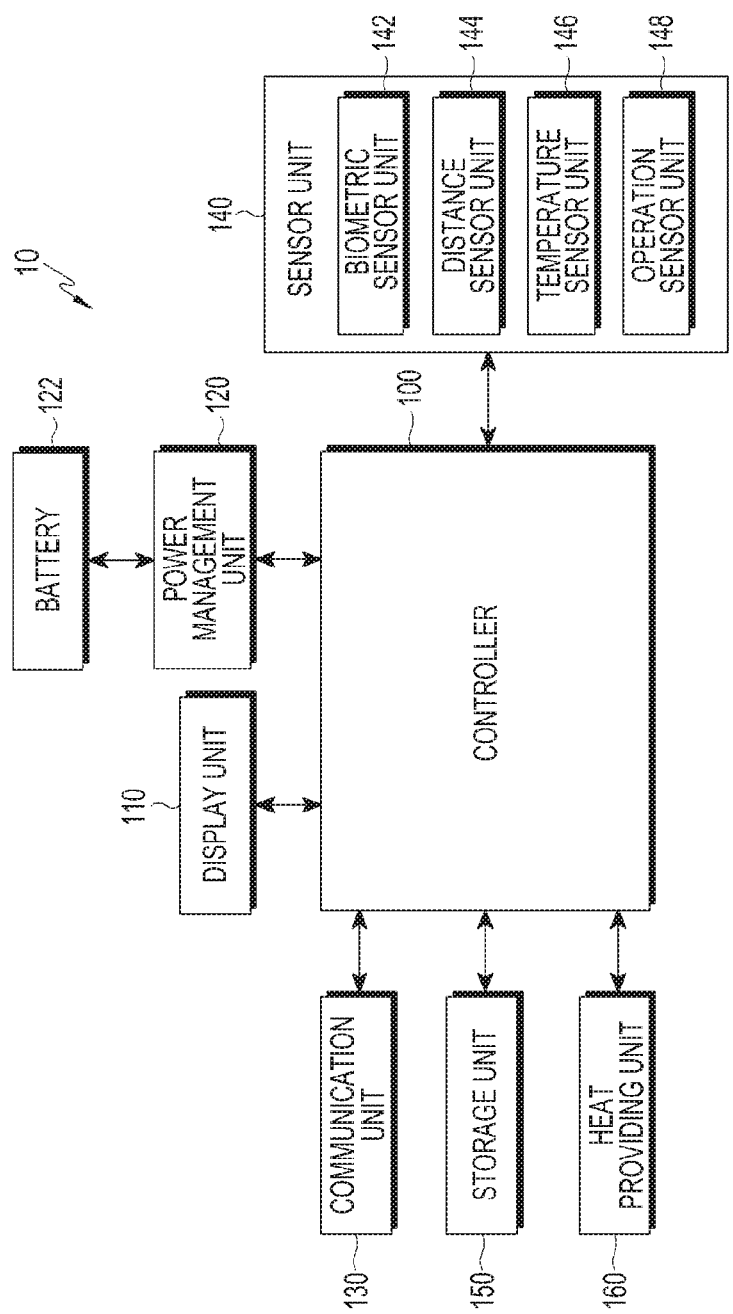
Figure 2C:
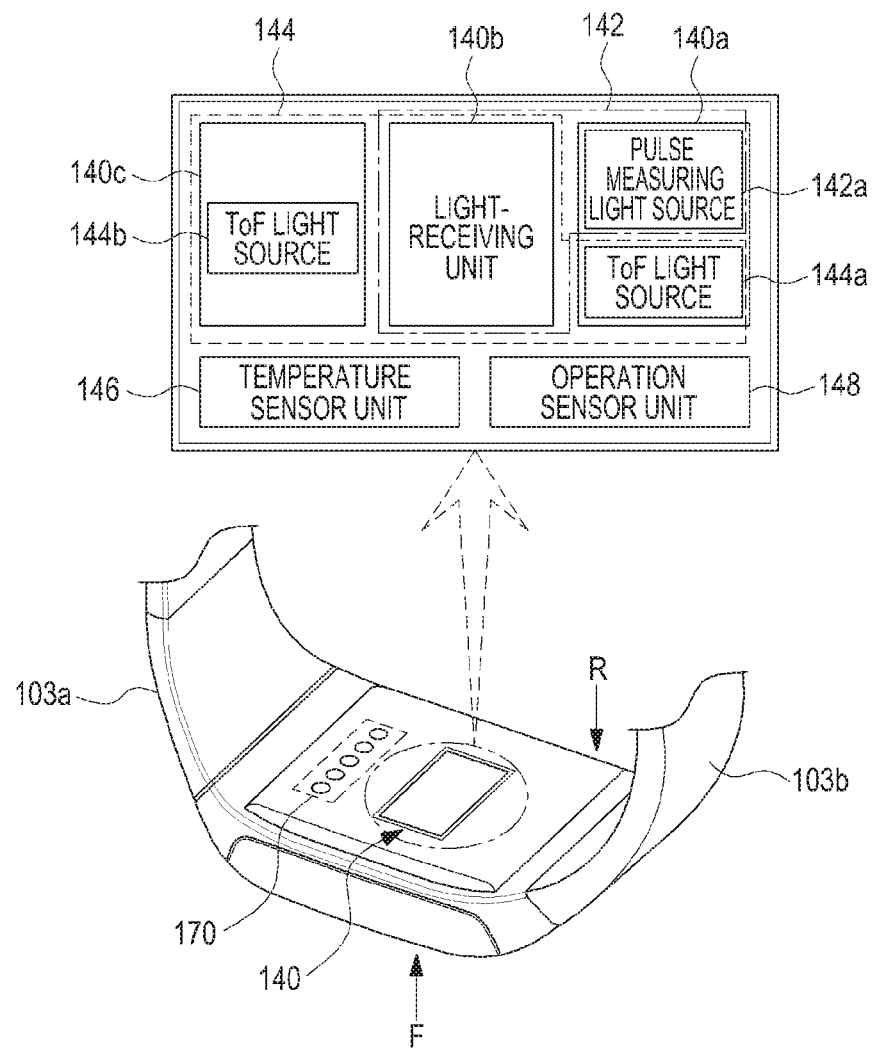

FIGS. 2A through 2C are exemplary diagrams for describing a structure of a wearable device according to various embodiments of the present disclosure.

Referring to FIG. 2A, the wearable device 10 according to various embodiments of the present disclosure may be, for example, an electronic device that is wearable on a wrist such as a watch or a bracelet. However, a shape of the wearable device 10 is not limited to that shown in FIG. 2A, and may also be manufactured as a communication device or medical equipment. The wearable device 10 according to various embodiments of the present disclosure may be worn on a body part such as, for example, a wrist or an ankle.

The wearable device 10 according to various embodiments of the present disclosure may include a main body portion 101 and a wearing portion 102. The main body portion 101 may include a front surface F, and a rear surface R that contacts the body of the user 20 wearing it. The display unit 110 is disposed on the front surface F of the main body portion 101. As will be described below, a sensor unit 140 according to various embodiments of the present disclosure is disposed on the rear surface R of the main body portion 101. The main body portion 101 may be formed to generally fit the body of a user 20.

The wearing portion 102 may include a first wearing member 103a and a second wearing member 103b. The second wearing member 103b may include multiple binding holes 104. The multiple binding holes 104 may be arranged so that the first wearing member 103a and the second wearing member 103b can be adjusted to fit a body part of the user 20.

Referring to FIG. 2B, the wearable device 10 according to various embodiments of the present disclosure may include a controller 100, the display unit 110, a power management unit 120, a battery 122, a communication unit 130, the sensor unit 140, a storage unit 150, and a heat providing unit 160.

The controller 100 may include one or more of a central processing unit (CPU), an application processor (AP), a communication processor (CP), and/or a micro controller unit (MCU). The controller 100 may perform, for example, operations or data processing associated with control and/or communication of at least one other element of the wearable device 10.

The display unit 110 may include a panel, a hologram device, or a projector. The panel may include, for example, a liquid crystal display (LCD) or an active matrix organic light-emitting diode (AM-OLED). The panel may be flexible, transparent, and/or wearable. The panel may be integrally formed with a touch panel as one unit. The touch panel may recognize a touch input of at least one of a capacitive type, a resistive type, an infrared type, and an ultrasonic wave type. The touch panel may further include a control circuit. For the capacitive type, a physical contact or proximity may be recognized. The touch panel may further include a tactile layer. In this case, the touch panel may provide a tactile reaction to the user. The hologram device shows a stereoscopic image over the air by using interference of light. The projector displays an image by projecting light onto a screen. The screen may be disposed, for example, on or outside the wearable device 10. According to various embodiments of the present disclosure, the display unit 110 may further include a control circuit for controlling the panel, the hologram device, and/or the projector.

The power management unit 120 manages power of the wearable device 10. Although not shown, the power management unit 120 may include, for example, a power management integrated circuit (PMIC), a charger IC, or a battery gauge. The PMIC is mounted, for example, in the IC or a system on chip (SoC) semiconductor. The charging scheme may be classified into a wired type and a wireless type. The charger IC charges the battery 122 and prevents introduction of over-voltage or over-current from a charging device. According to an embodiment, the charger IC may include a charger IC for at least one of the wired charging type and the wireless charging type. The wireless charging type may include, for example, a magnetic resonance type, a magnetic induction type, and an electromagnetic type, and an additional circuit for wireless charging, e.g., a coil loop, a resonance circuit, or a rectifier may be used by the wireless charging type.

The battery gauge measures, for example, the remaining capacity, a voltage, current, and/or temperature of the battery 122. The battery 122 stores electricity and supplies power to the wearable device 10 by using the stored electricity. The battery 122 may include, for example, a rechargeable battery or a solar battery. The solar battery may comprise solar cells to generate electricity to charge itself and/or supply electricity to the device it is in.

The communication unit 130 performs data transmission and reception between the wearable device 10 and another external electronic device (e.g., a smartphone) connected with the wearable device 10 through wired/wireless communication. According to various embodiments of the present disclosure, the communication unit 130 may include a universal serial bus (USB) unit, a WiFi unit, a Bluetooth (BT) unit, a near field communication (NFC) unit, a global positioning system (GPS) unit, and so forth. According to various embodiments of the present disclosure, at least three of the USB unit, the WiFi unit, the BT unit, the NFC unit, and the GPS unit may be included in one IC or IC package.

The sensor unit 140 measures a physical amount or senses an operation state of the wearable device 10 to convert the measured or sensed information into an electric signal. The sensor unit 140 may include at least one of a biometric sensor unit 142, a distance sensor unit 144, a temperature sensor unit 146, and an operation sensor unit 148.

The biometric sensor unit 142 may be configured to perform a function/operation of sensing (or obtaining) various biometric information (e.g., a pulse rate, an oxygen saturation, and so forth) of the user 20. Herein, pulse rate, oxygen saturation, and/or the amount of calories consumed have been mentioned as examples of the biometric information of the user 20, but they are used for convenience and embodiments of the biometric information are not limited by these examples. That is, the biometric information according to various embodiments of the present disclosure may further include various biometric information such as pulse, temperature, electrocardiogram, body fat percentage, activity level, and pressure.

The distance sensor unit 144 is configured to perform a function/operation of sensing a distance between a body part (e.g., a wrist) of the user 20 and the wearable device 10 (or obtaining information about the distance) if the wearable device 10 worn on the user 20 moves (or is shaken) due to motion of the user 20.

The temperature sensor unit 146 is configured to perform a function/operation of sensing a skin temperature of a body part of the user 20 (e.g., the wrist of the user 20 on which the wearable device 10 is worn) (or obtaining information about the skin temperature of the user 20). The term "pulse rate" may be interchangeably used with various terms such as a "pulse cycle" or a "heart rate" according to embodiments.

The operation sensor unit 148 is configured to perform a function/operation of sensing motion of the user 20. The operation sensor unit 148 may include, for example, an acceleration sensor. The sensor unit 140 additionally or alternatively may include an e-noise sensor, an electromyography (EMG) sensor, an electroencephalogram (EEG) sensor, an electrocardiogram (ECG) sensor, an infrared (IR) sensor, an iris sensor, or a fingerprint sensor. The sensor unit 140 may further include a control circuit for controlling at least one sensor included therein.

The storage unit 150 may include volatile and/or non-volatile memory. The storage unit 150 stores commands or data associated with at least one other elements of the wearable device 10. According to various embodiments of the present disclosure, the storage unit 150 may store software and/or various programs.

The heat providing unit 160 is configured to perform a function/operation of providing heat to increase skin temperature of the user 20 if the skin temperature sensed by the temperature sensor unit 146 is equal to or less than a threshold temperature. With such a function/operation, noise generated by the skin temperature (that is, an error generated due to a low skin temperature) may be reduced when the temperature sensor unit 146 obtains a biometric measurement (e.g., the pulse rate) of the user 20. As will be described below, the heat providing unit 160 may include time of flight (ToF) light sources 144a and 144b, and the skin temperature of the body part of the user 20 (e.g., the wrist of the user 20 on which the wearable device 10 is worn) may be increased using a signal (e.g., infrared light) output from the ToF light sources 144a and 144b.

Referring to FIG. 2C, the sensor unit 140 and a charging terminal unit 170 are disposed on the rear surface R of the wearable device 10. The sensor unit 140 disposed on the rear surface R of the wearable device 10 may be interchangeably used with a term such as a "sensor interface" according to various embodiments of the present disclosure.

The biometric sensor unit 142 according to various embodiments of the present disclosure may include a light-receiving unit 140b and a pulse measuring light source 142a. The pulse measuring light source 142a outputs a signal (e.g., red light or IR light) for obtaining biometric information (e.g., the pulse rate or the oxygen saturation of arterial blood) of the user 20. However, the type of output signal is not limited to the above example, and the type of the signal output by the pulse measuring light source 142a may include various types of signals that may be sensed by the light-receiving unit 140b. The pulse measuring light source 142a may include a light-emitting diode (LED). The controller 100 determines the amount of consumed calories of the user 20 based on information about the obtained oxygen saturation. A way to determine the amount of consumed calories based on the oxygen saturation may use various conventional methods.

The light-receiving unit 140b senses the light (e.g., IR light) output from a light source and reflected from the body part of the user. The controller 100 determines a pulse rate and/or an oxygen saturation of the user 20 based on a change in the attribute of light sensed by the light-receiving unit 140b. A way to determine the pulse rate and/or the oxygen saturation based on the light sensed by the light receiving unit 140b may use various conventional methods.

The distance sensor unit 144 according to various embodiments of the present disclosure may include the ToF light sources 144a, 144b and the light-receiving unit 140b. The ToF light sources 144a and 144b are configured to output red light or IR light to sense a distance between the body part (e.g., the wrist) of the user 20 and the wearable device 10. However, the type of output light is not limited to the above example, and the type of light output from the ToF light sources 144a and 144b may include various types of light that may be sensed by the light-receiving unit 140b.

The temperature sensor unit 146 according to various embodiments of the present disclosure is configured to sense a skin temperature of the body part of the user 20 adjacent to the wearable device 10 when the wearable device 10 is worn by the user 20. The skin temperature may be measured in a non-contact manner using, for example, IR light.

The operation sensor unit 148 according to various embodiments of the present disclosure is configured to determine whether the user 20 moves. As mentioned above, the operation sensor unit 148 may include an acceleration sensor.

Viewed from another aspect, the sensor unit 140 according to various embodiments of the present disclosure may include the first light source unit 140a, the light-receiving unit 140b, and a second light source unit 140c. The first light source unit 140a may include the pulse measuring light source 142a and the ToF light source 144a. The second light source unit 140c may include the second ToF light source 144b. However, according to various embodiments of the present disclosure, one of the ToF light source 144a and the ToF light source 144b may be omitted. That is, the wearable device 10 according to various embodiments of the present disclosure may include at least one ToF light sources.

FIGS. 3A through 3E are exemplary diagrams for describing a function/operation of determining whether a wearable device is worn on a user according to various embodiments of the present disclosure.

Figure 3A:
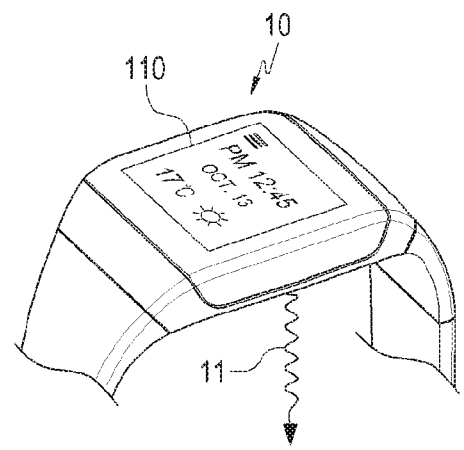
FIGS. 3A through 3E are exemplary diagrams for describing a function/operation of determining whether a wearable device is worn by a user according to various embodiments of the present disclosure.
Figure 3B:
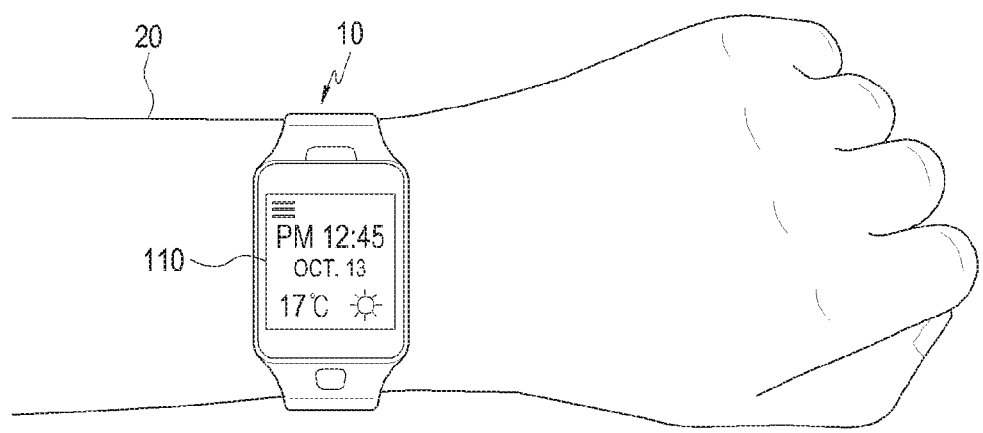

Referring to FIG. 3A, the controller 100 controls the ToF light source 144a or the ToF light source 144b to output a wearing sensing signal 11 (e.g., IR light) to determine whether the user 20 wears the wearable device 10 as illustrated in FIG. 3B.

Figure 3C:
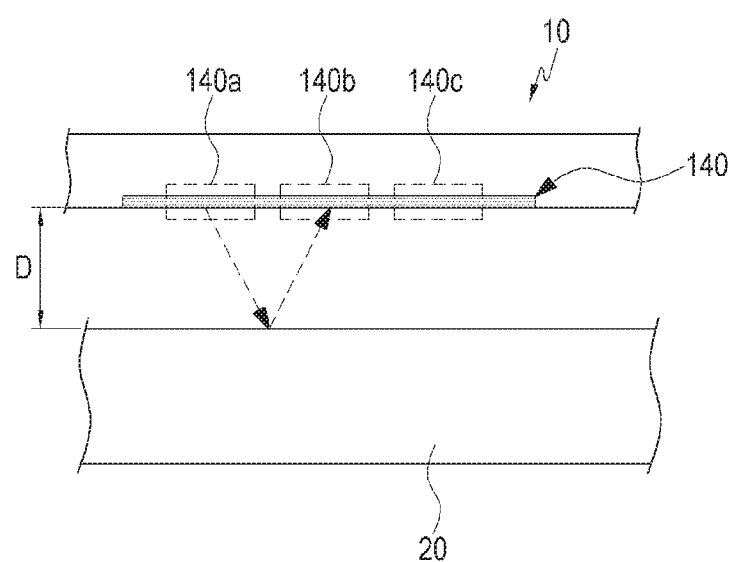

Referring to FIG. 3C, the controller 100 may determine that the wearable device 10 is worn on the user 20 if the wearing sensing signal 11 output from the first light source unit 140a is sensed by the light-receiving unit 140b. Once the controller 100 determines that the wearable device 10 is being worn by the user 20, the controller 100 controls the pulse measuring light source 142a of the first light source unit 140a to output a signal for obtaining biometric information of the user 20.

Figure 3D:
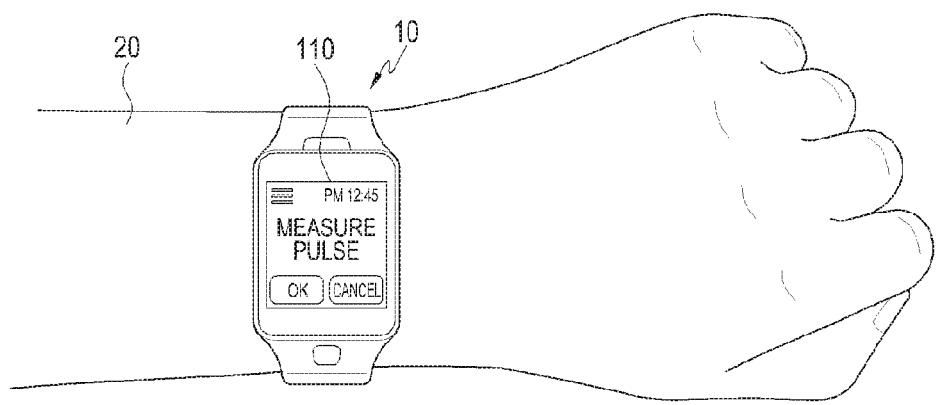
Figure 3E:
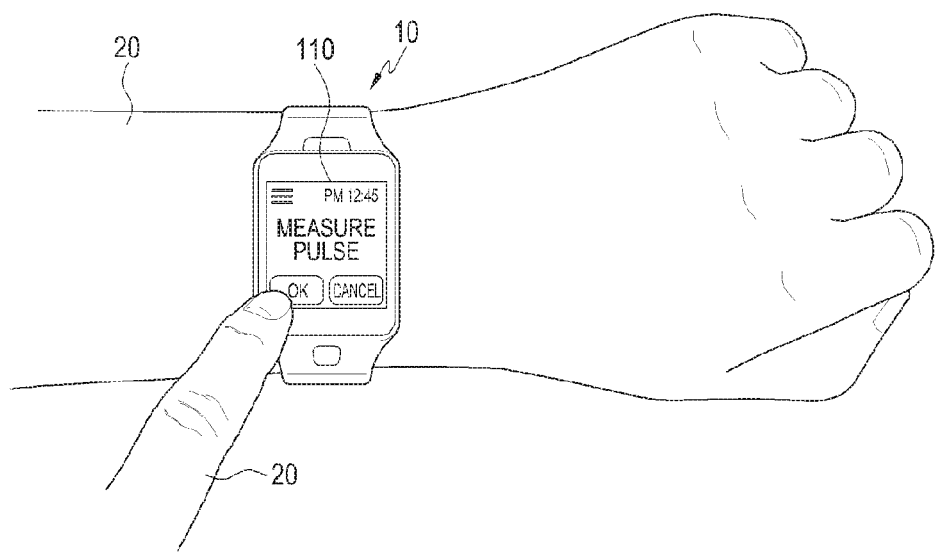

Referring to FIGS. 3D and 3E, according to a different embodiment than illustrated in FIGS. 3A through 3C, an input from the user 20 as illustrated in FIG. 3E initiates the controller 100 to control the pulse measuring light source 142a of the first light source unit 140a to output a signal for obtaining the biometric information of the user 20.

FIGS. 4A through 4H are exemplary diagrams for describing a function/operation of obtaining biometric information (e.g., a heart rate) of a user at a wearable device by considering motion of the user according to various embodiments of the present disclosure.

Figure 4A:
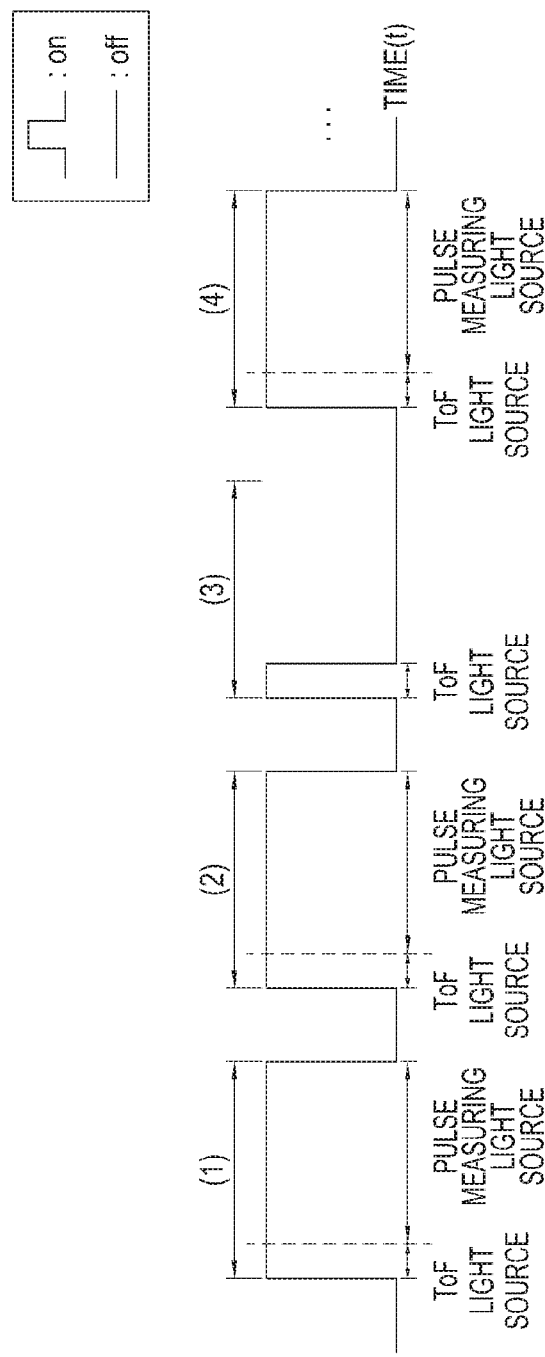
FIGS. 4A through 4H are exemplary diagrams for describing a function/operation of obtaining biometric information (e.g., a heart rate) of a user at a wearable device by considering the user's motions according to various embodiments of the present disclosure.

Referring to FIG. 4A, upon sensing the user 20 wearing the wearable device 10, the controller 100 controls the ToF light sources 144a and 144b in the first light source unit 140a and the second light source unit 140c, respectively, to output a signal to determine a distance between a body part of the user 20 and the wearable device 10. The controller 100 determines as a reference distance D the distance between the wearable device 10 and the user 20 when wearing of the wearable device 10 is initially sensed (section (1) of FIG. 4A). That is, the controller 100 determines an initial distance between the wearable device 10 and the user 20, which is determined in the section (1) of FIG. 4A, as the reference distance D. This reference distance D may be used in the process of obtaining the biometric information of the user 20.

Figure 4B:
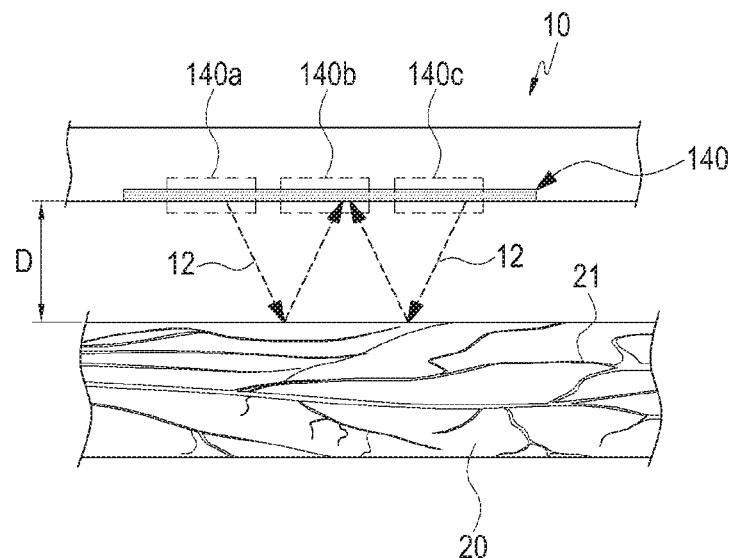
Figure 4C:
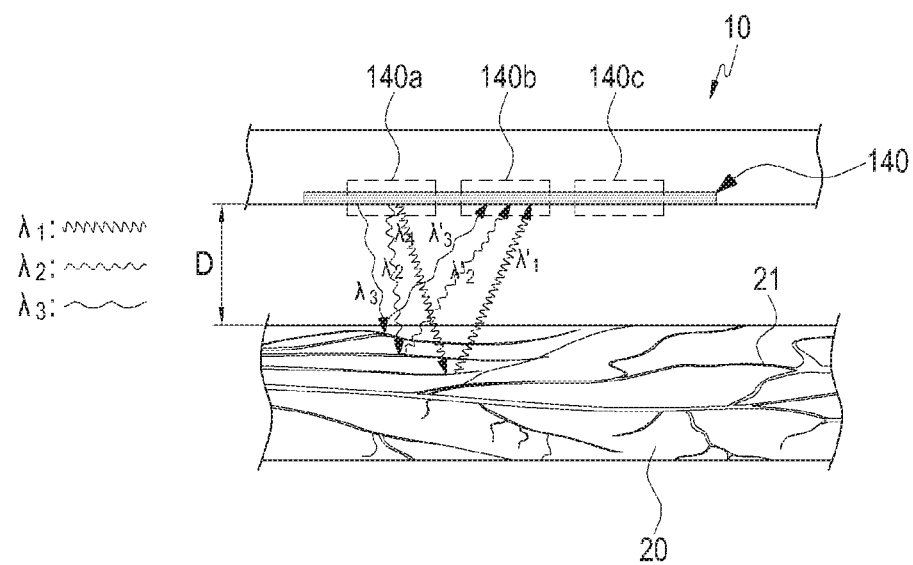
Figure 4D:

In section (2) of FIG. 4A, if the wearable device 10 moves due to motion of the user 20 (e.g., as illustrated in FIG. 4D), there may be a new distance D1 measured between the wearable device 10 and the user 20 that is equal to or less than the reference distance D. In section (2) of FIG. 4A, since the distance D1 between the wearable device 10 and the user 20 is equal to or less than the reference distance D, the controller 100 may control the pulse measuring light source 142a to output a signal to measure a pulse of the user 20.

While the distance (e.g., D1) between the wearable device 10 and the user 20 may be determined using the ToF light source 144a, this is merely an example for describing the present disclosure. The distance between the wearable device 10 and the user 20 may also be determined by using the second ToF light source 144b. Accordingly, any appropriate light source may be controlled to output a signal to determine the distance between the wearable device 10 and the user 20, thereby accurately determining motion of the user 20. According to various embodiments of the present disclosure, the operation sensor unit 148 may also be used to sense whether the user 20 may be moving.

Figure 4E:
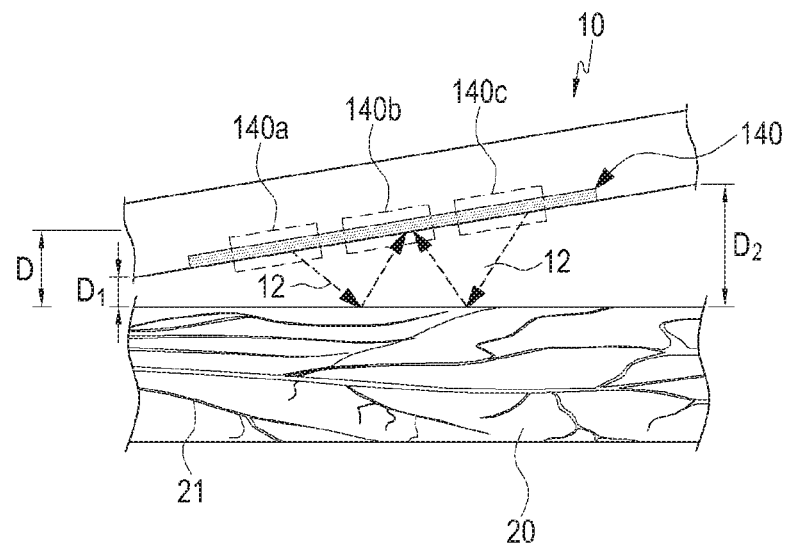
Figure 4F:
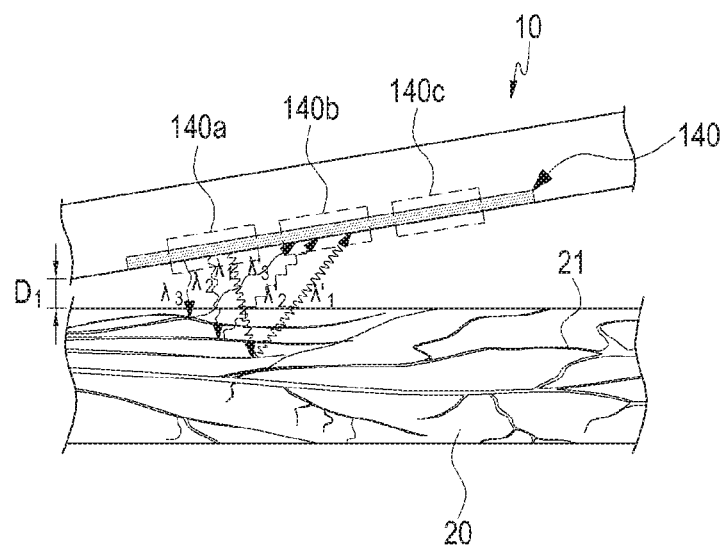
Figure 4G:
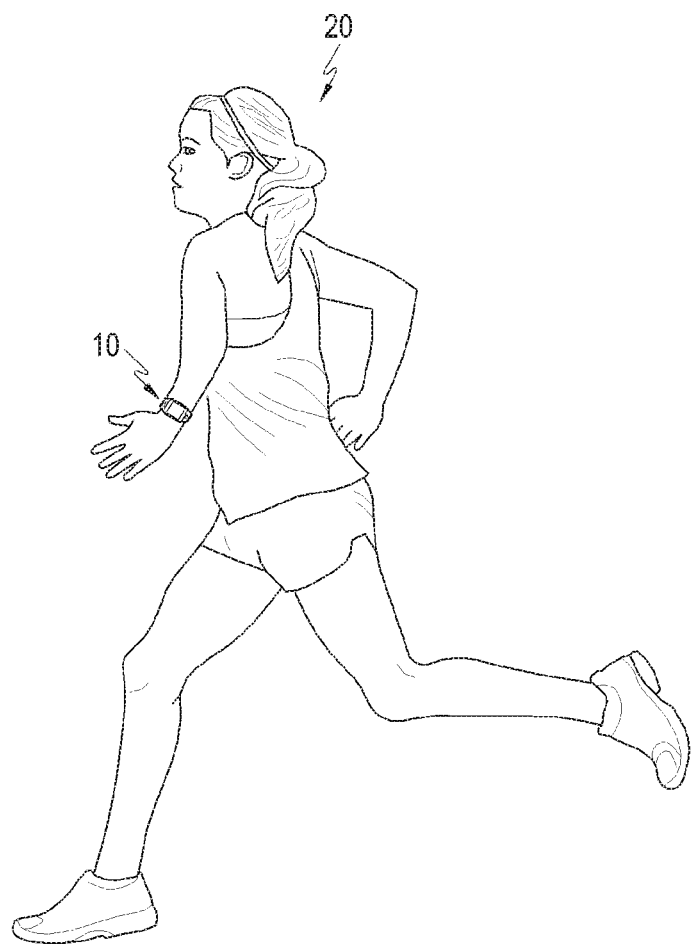

In section (3) of FIG. 4A, if the wearable device 10 moves due to motion of the user 20 (e.g., as illustrated in FIG. 4G), the distance D1 between the wearable device 10 and the user 20 may exceed the reference distance D. Accordingly, the controller 100 may control the pulse measuring light source 142a to not output a signal to measure the pulse of the user 20. That is, the controller 100 controls the pulse measuring light source 142a to output the signal if determining that the first light source unit 140a including the pulse measuring light source 142a is in proximity with a body part of the user 20, and reduces noise caused by motion of the user 20 and also power consumption in measurement of the biometric information.

In section (4) of FIG. 4A, as in section (2) of FIG. 4A, the distance D1 between the wearable device 10 and the user 20 returns to being equal to or less than the reference distance D due to motion of the user 20, such that the function/operation of obtaining the biometric information of the user 20 is performed.

Referring to FIG. 4B, upon sensing that the wearable device 10 is on the user 20, the controller 100 controls the ToF light sources 144a and 144b of the first light source unit 140a and the second light source unit 140c, respectively, to output a signal 12 to determine the distance D between the wearable device 10 and the user 20. The controller 100 sets the determined distance D as a reference distance. FIG. 4B further illustrates section (1) of FIG. 4A in which the signal 12 is output by the ToF light sources 144a and 144b. The controller 100 controls the ToF light sources 144a and 144b to output the signal 12 to determine the distance at preset time intervals (or preset periods).

Referring to FIG. 4C, when the distance between the wearable device 10 and the user 20 maintains the reference distance D, the controller 100 controls the pulse measuring light source 142a to output various signals $\lambda 1$, $\lambda 2$, and $\lambda 3$ to obtain the biometric information of the user 20. Signals $\lambda'1$, $\lambda'2$, and $\lambda'3$, which are the signals $\lambda 1$, $\lambda 2$, and $\lambda 3$ reflected from a blood vessel 21 of the user 20, are received by the light-receiving unit 140b. The controller 100 may obtain various biometric information such as, for example, pulse rate and/or oxygen saturation of the user 20, based on a change in attribute (e.g., wavelength) of the signals $\lambda'1$, $\lambda'2$, and $\lambda'3$ compared to the signals $\lambda 1$, $\lambda 2$, and $\lambda 3$. A way to obtain the pulse rate and/or the oxygen saturation of the user 20 based on the change in attribute of the received signals $\lambda'1$, $\lambda'2$, and $\lambda'3$ may use various conventional methods. Each of the signals $\lambda 1$, $\lambda 2$, and $\lambda 3$ may have different wavelengths. Although three signals $\lambda 1$, $\lambda 2$, and $\lambda 3$ having different wavelengths are illustrated in FIG. 4C, various embodiments need not be limited so. Other embodiments may have different number of signals with their respective wavelengths.

Referring to FIG. 4D, the wearable device 10 worn by the user 20 may move due to motions of the user 20. In FIG. 4E, due to motions of the user 20 as illustrated in FIG. 4D, the distance between the wearable device 10 and the user 20 is changed to D1 that is less than the reference distance D. As mentioned above, the distance may be determined based on the first light source unit 140a. If the distance between the wearable device 10 and the user 20 is equal to or less than the reference distance D as illustrated in FIG. 4E, the controller 100 controls the signals $\lambda 1$, $\lambda 2$, and $\lambda 3$ to be output as illustrated in FIG. 4F to obtain the biometric information of the user 20. The description regarding FIGS. 4E and 4F may correspond to the description of section (2) of FIG. 4A.

Figure 4H:
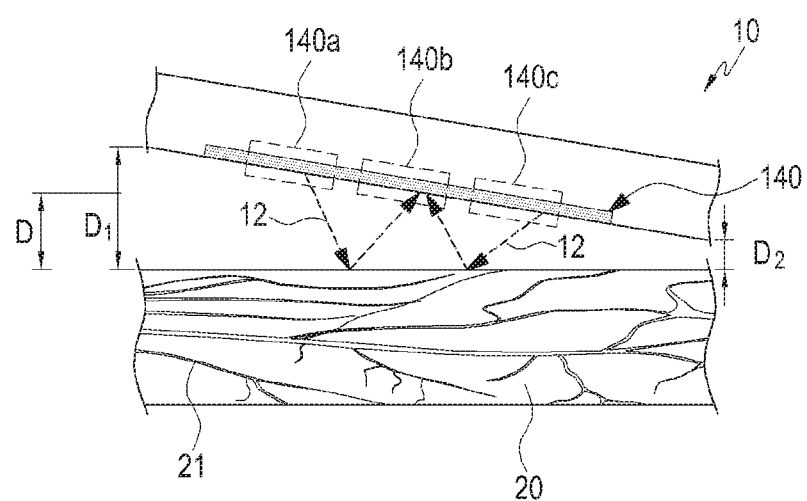

Referring to FIGS. 4G and 4H, the distance D1 between the wearable device 10 and the user 20 now exceeds the reference distance D due to motion of the user 20. Accordingly, the controller 100 controls the signals $\lambda 1$, $\lambda 2$, and $\lambda 3$ to not be output, and, therefore, no biometric information will be collected at this time. The description regarding FIGS. 4G and 4H may correspond to the description of the section (3) of FIG. 4A.

Figure 5:
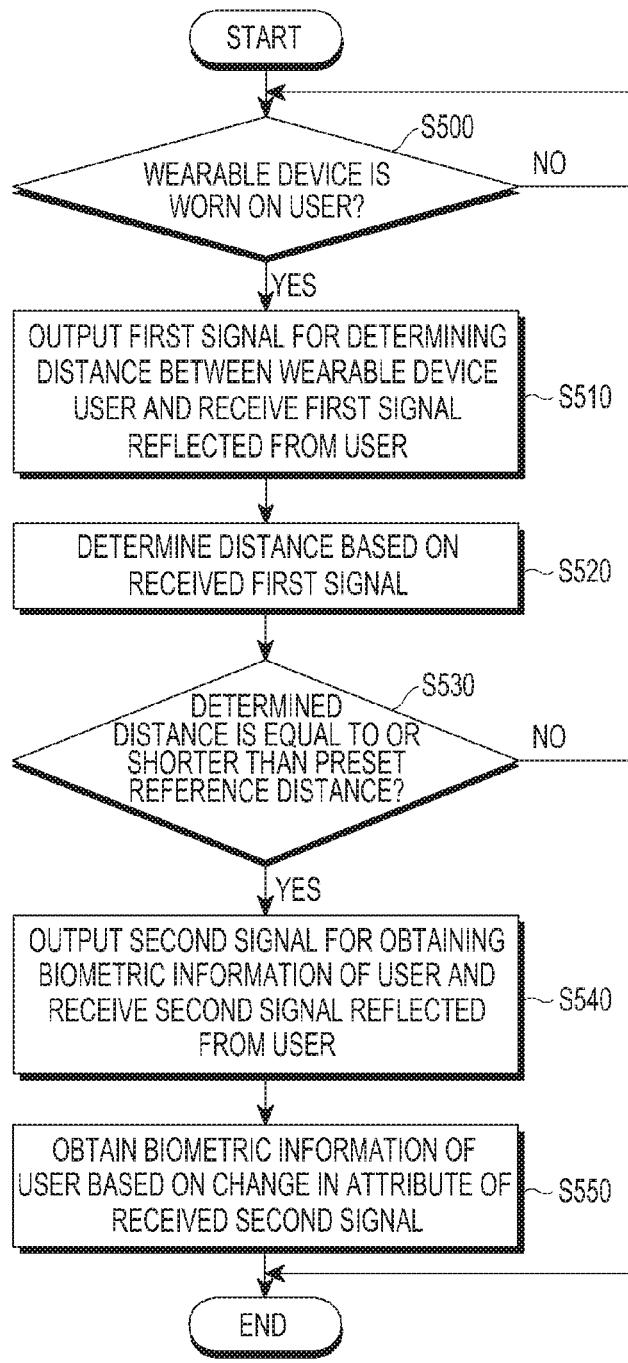
FIG. 5 is a diagram for describing a method for controlling a wearable device according to various embodiments of the present disclosure.

FIG. 5 is a diagram for describing a method for controlling a wearable device according to various embodiments of the present disclosure.

Referring to FIG. 5, a method for controlling the wearable device 10 according to various embodiments of the present disclosure may include an operation S500 of determining whether the wearable device 10 is worn by the user 20. If the wearable device 10 is on the user 20, a first signal for determining a distance between the wearable device 10 and the user 20 is output and the first signal reflected from the user 20 is received in operation S510. The wearable device 10 determines the distance based on the received first signal in operation S520, and determines whether the determined distance is equal to or less than the reference distance in operation S530. If the determined distance is equal to or less than the reference distance, the wearable device 10 outputs a second signal to obtain biometric information of the user 20 and receives the second signal reflected from the user 20 in operation S540. The wearable device 10 obtains the biometric information of the user 20 based on a change in attribute of the received second signal in operation S550.

This method for controlling the wearable device 10 may be applied to various embodiments of the disclosure. However, an embodiment need not be limited to this method. Various other methods may be used to control the wearable device 10.

FIGS. 6A through 6D are exemplary diagrams for describing a function/operation of obtaining biometric information of a user by a wearable device by considering the current body condition of the user according to various embodiments of the present disclosure.

Figure 6A:
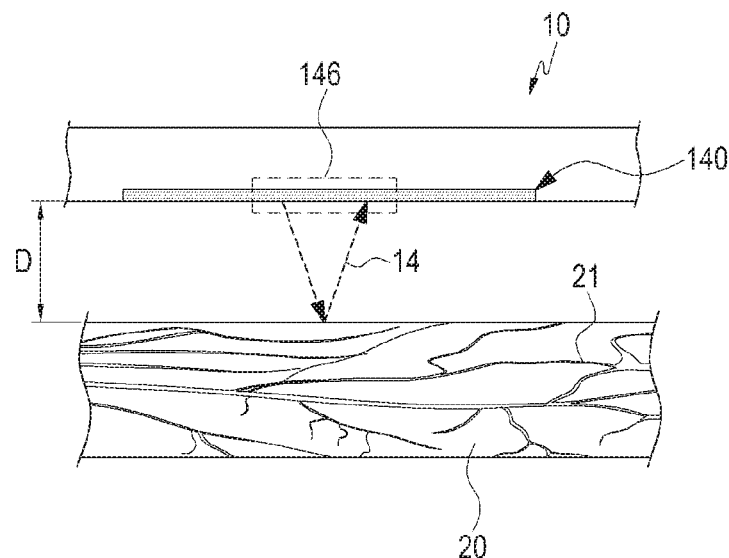
FIGS. 6A through 6D are exemplary diagrams for describing a function/operation of obtaining biometric information of a user by a wearable device by considering the user's current body condition according to various embodiments of the present disclosure.

Referring to FIG. 6A, the controller 100 senses a current body condition (e.g., the current skin temperature) of the user 20 using the temperature sensor unit 146. For example, for the skin temperature as the current body condition, the temperature sensor unit 146 receives IR light reflected from the skin of the user 20 and senses the current skin temperature of the user 20. To output the IR light, the temperature sensor unit 146 may include a temperature sensor light source (not shown). The current skin temperature of the user 20 may be measured in a contact and/or non-contact manner using various conventional methods.

Figure 6B:
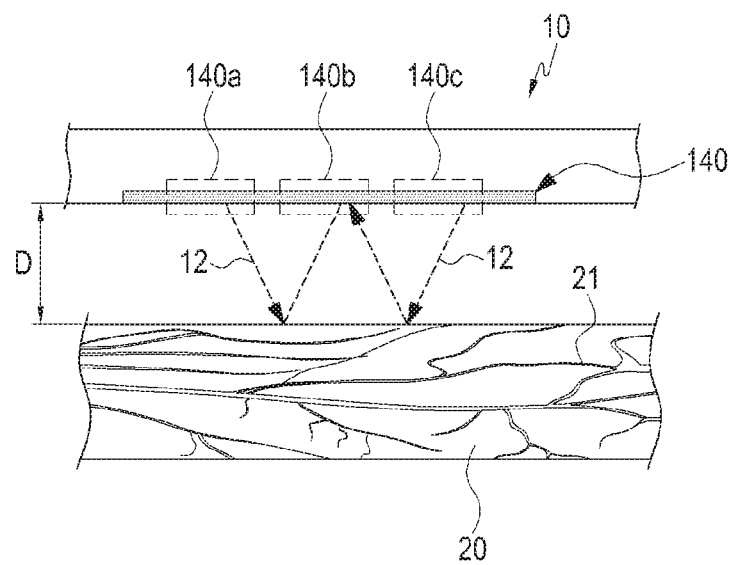

Referring to FIG. 6B, if the sensed skin temperature of the user 20 is equal to or less than a preset skin temperature (referred to as a "reference temperature"), the controller 100 controls the heat providing unit 160 to output light (e.g., red light or IR light) to increase the skin temperature. A position at which the skin temperature is sensed and a position to which the light for increasing the skin temperature is output may globally coincide with a position to which the second signal (FIG. 5) is output to obtain the biometric information.

The heat providing unit 160 (FIG. 2B) may include at least one of the ToF light sources 144a and 144b. Accordingly, the light output by the ToF light sources 144a and 144b may be used to increase the skin temperature at certain times as well as to determine distance at other times. By warming the skin to be sensed for biometric information, it is possible to reduce inaccurate sensing when the skin temperature was too low to sense for proper biometric information. The reference temperature may be in a predetermined temperature range that is suitable for obtaining the biometric information with the second signal.

Figure 6C:
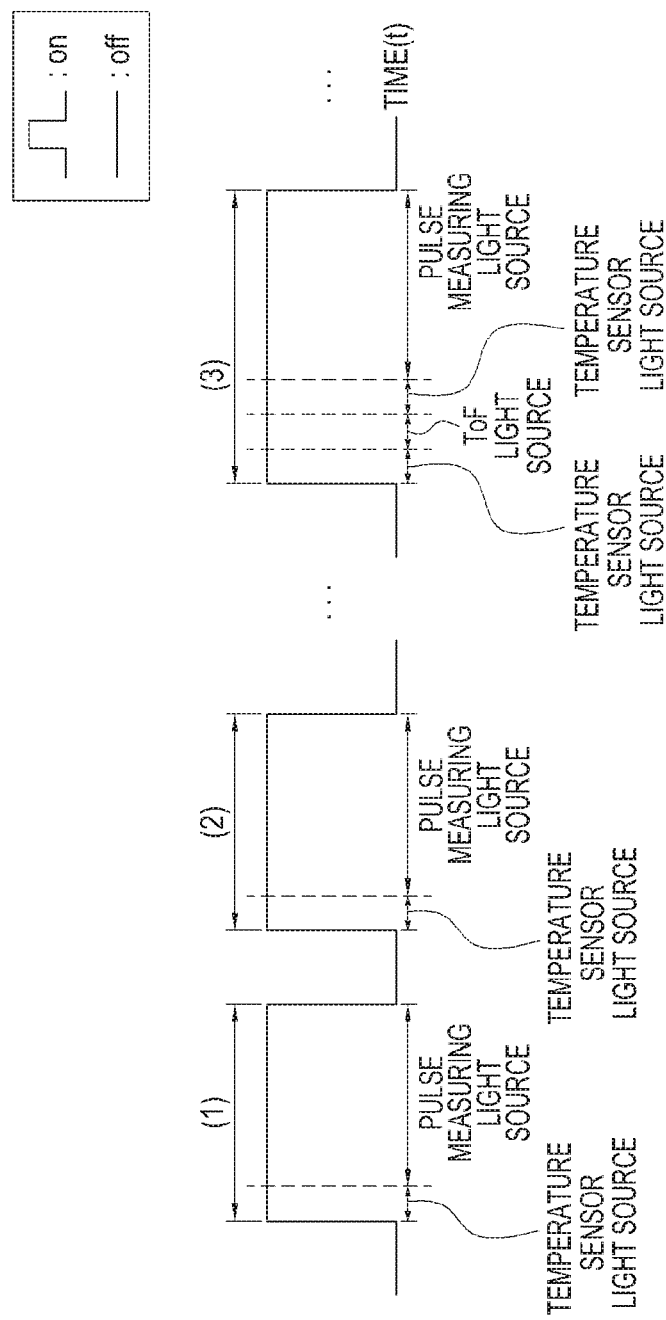

Referring to FIG. 6C, the controller 100 controls the temperature sensor unit 146 to sense the skin temperature of the user 20 as described in relation to FIG. 6A. The controller 100 controls the temperature sensor light source to output the IR light to sense the skin temperature at preset time intervals. If the skin temperature exceeds the reference temperature, the controller 100 controls the biometric sensor unit 142 to output light to obtain biometric information (e.g., the pulse rate of the user 20) (in sections (1) and (2) of FIG. 6C). However, if the skin temperature is equal to or less than the reference temperature, the controller 100 controls the heat providing unit 160 to output light to increase the skin temperature. In FIG. 6C, as an embodiment of the heat providing unit 160, the ToF light sources 144a and 144b are controlled to output the light (in section (3) of FIG. 6C). After warming the skin, the controller 100 controls the temperature sensor light source to output the IR light to sense the skin temperature. If the skin temperature exceeds the reference temperature, the controller 100 controls the biometric sensor unit 142 to output light to obtain biometric information.

Figure 6D:
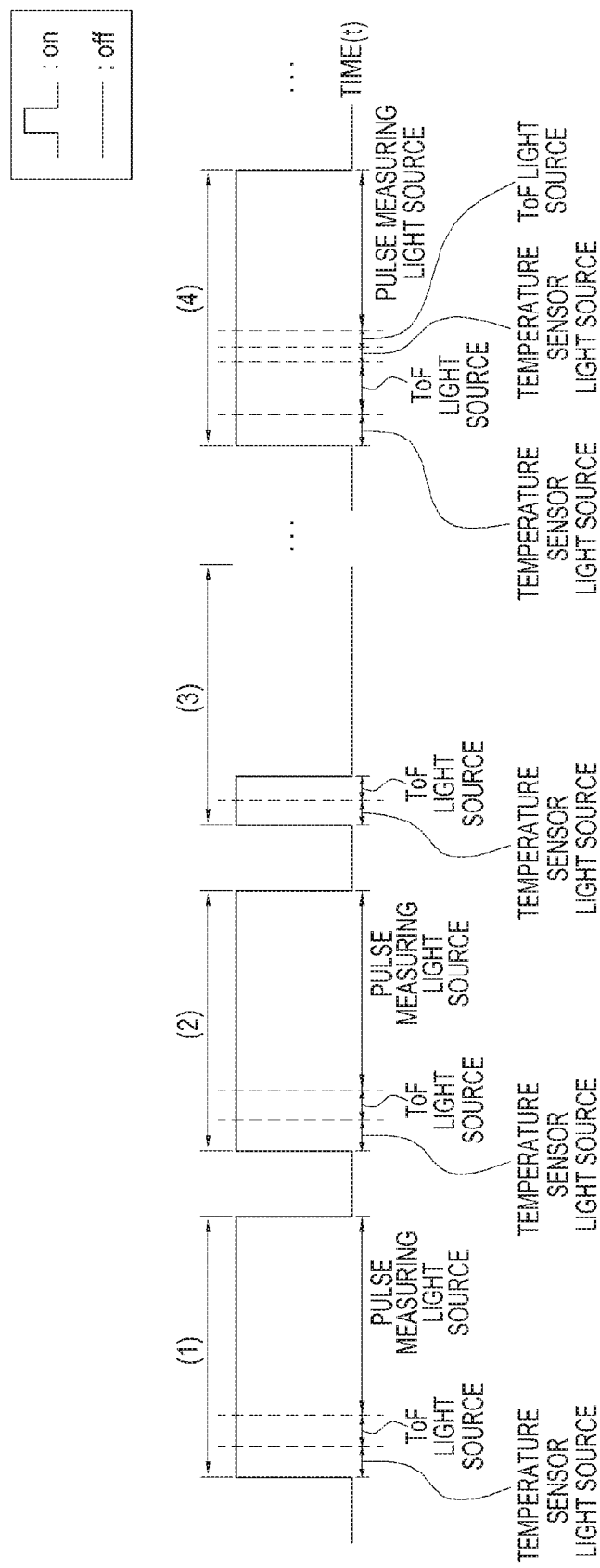

FIG. 6D shows an embodiment in which the embodiment described with reference to FIG. 4A and the embodiment described with reference to FIG. 6C are combined.

In a section (1) of FIG. 6D, the skin temperature is equal to or greater than the reference temperature and the distance D1 is equal to the reference distance D. In this case, the controller 100 may control, for example, the pulse measuring light source 142a to output light to obtain the user's biometric information.

In a section (2) of FIG. 6D, the skin temperature is equal to or greater than the reference temperature and the distance D1 is equal to or less than the reference distance D. In this case, the controller 100 may control, for example, the pulse measuring light source 142a to output light to obtain the user's biometric information.

In a section (3) of FIG. 6D, the skin temperature is equal to or greater than the reference temperature and the distance D1 exceeds the reference distance D. In this case, the controller 100 may control, for example, the pulse measuring light source 142a to not output light.

In a section (4) of FIG. 6D, the skin temperature is equal to or less than the reference temperature and the distance D1 is less than the reference distance D. In this case, the controller 100 may control the ToF light sources 144a and 144b to output light to increase the skin temperature of the user 20 to the reference temperature or higher. After the light is output for a preset time, the controller 100 controls the temperature sensor unit 146 to sense the skin temperature again. In this case, if the re-sensed skin temperature is equal to or greater than the reference temperature, the controller 100 controls the biometric information to be obtained as shown in the section (4) of FIG. 6D.

Figure 7:
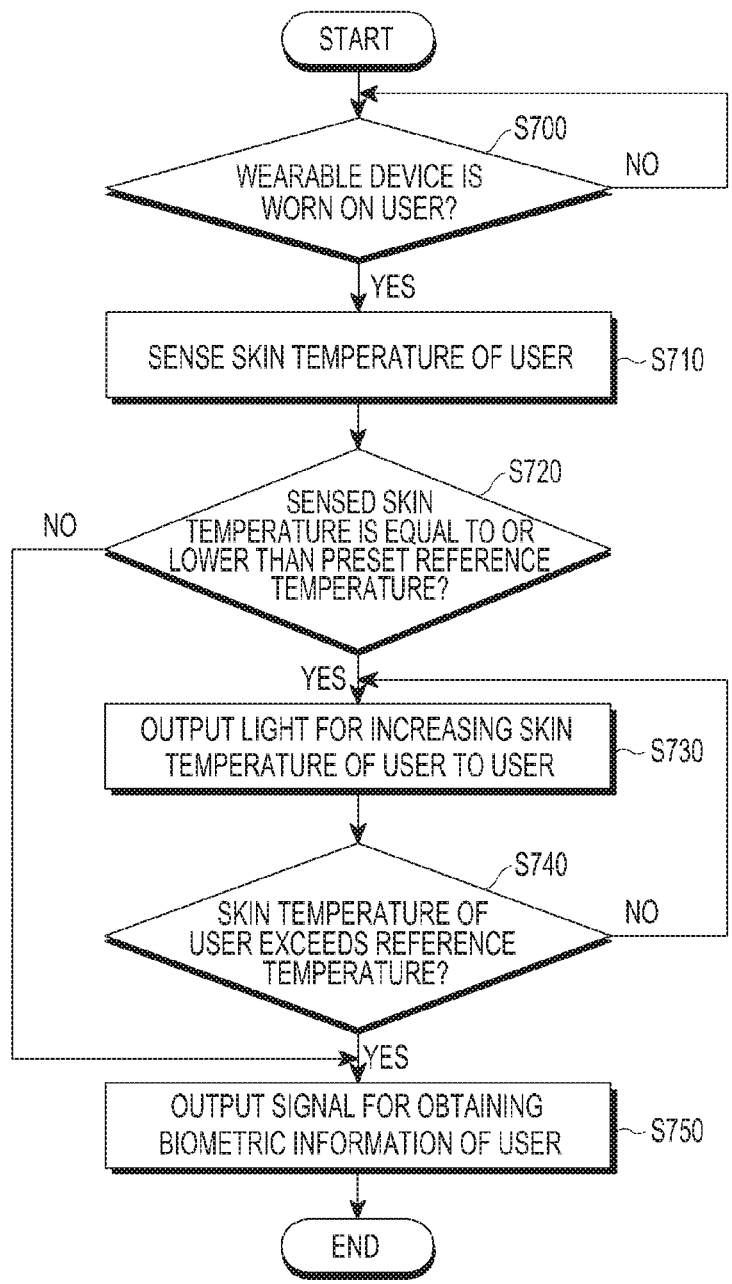
FIG. 7 is an exemplary diagram for describing a method for controlling a wearable device according to various embodiments of the present disclosure.

FIG. 7 is an exemplary diagram for describing a method for controlling a wearable device according to various embodiments of the present disclosure.

Referring to FIG. 7, a method for controlling a wearable device according to various embodiments of the present disclosure may include an operation S700 of determining whether the wearable device 10 is worn by the user 20. If the wearable device 10 is worn by the user 20, the wearable device 10 senses the skin temperature of the user 20 in operation S710. The wearable device 10 determines whether the sensed skin temperature is equal to or less than a preset temperature in operation S720, and if the sensed skin temperature is equal to or less than the preset temperature, light for increasing the skin temperature of the user 20 is output to the user 20 in operation S730. Once the light is output for the preset time, the wearable device 10 re-senses the skin temperature of the user 20 to determine whether the skin temperature of the user 20 exceeds the reference temperature in operation S740. If the re-sensed skin temperature of the user 20 is greater than the reference temperature, the wearable device 10 outputs a signal (e.g., the second signal) to obtain the user's biometric information in operation S750.

This method for controlling the wearable device 10 may be applied to various embodiments of the disclosure. However, an embodiment need not be limited to this method. Various other methods may be used to control the wearable device 10.

Figure 8A:
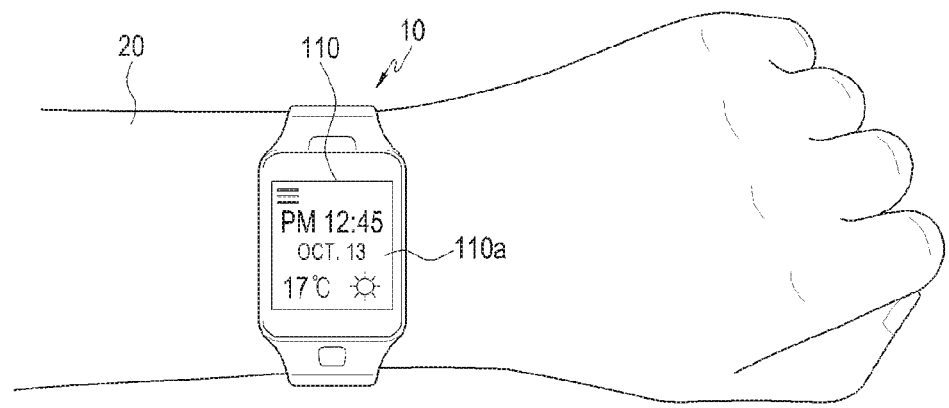
FIGS. 8A through 8C are exemplary diagrams for describing a function/operation of displaying on a wearable device the user's biometric information (e.g., a pulse rate and the amount of calories consumed) according to various embodiments of the present disclosure.
Figure 8B:
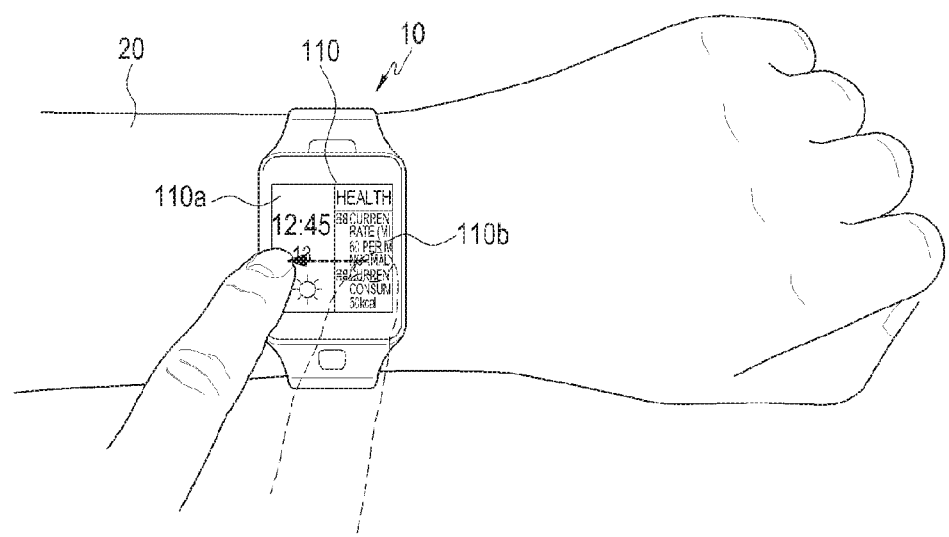
Figure 8C:
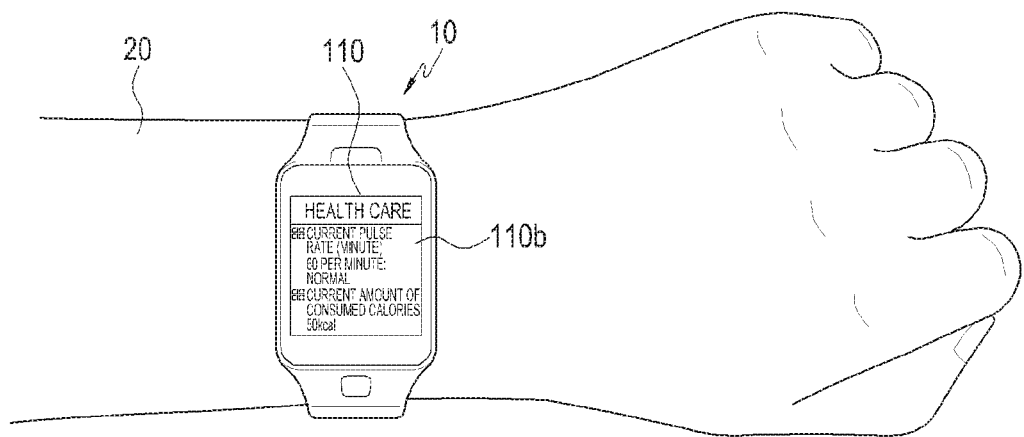

FIGS. 8A through 8C are exemplary diagrams for describing a function/operation of providing biometric information (e.g., a pulse rate and the amount of calories consumed) of the user to the user at a wearable device according to various embodiments of the present disclosure.

Referring to FIG. 8A, when the wearable device 10 is worn on a body part of the user 20, a home screen 110a is displayed on the display unit 110.

Referring to FIG. 8B, when the home screen 110a is displayed on the display unit 110, the wearable device 10 receives a drag input with respect to the home screen 110a as a screen switchover request to display a biometric information providing screen 110b for the user 20. The drag input is an example for a description of the present disclosure, and various other input gestures may be used for screen switchover.

Referring to FIG. 8C, in response to the screen switchover request, the controller 100 controls the biometric information providing screen 110b to be displayed on the display unit 110. In FIG. 8C, a current pulse rate and a current amount of consumed calories are shown as examples of the biometric information.

FIGS. 9A through 9D are exemplary diagrams for describing a function/operation of providing related information to a user if obtained biometric information of the user exceeds a preset threshold value according to various embodiments of the present disclosure.

Figure 9A:
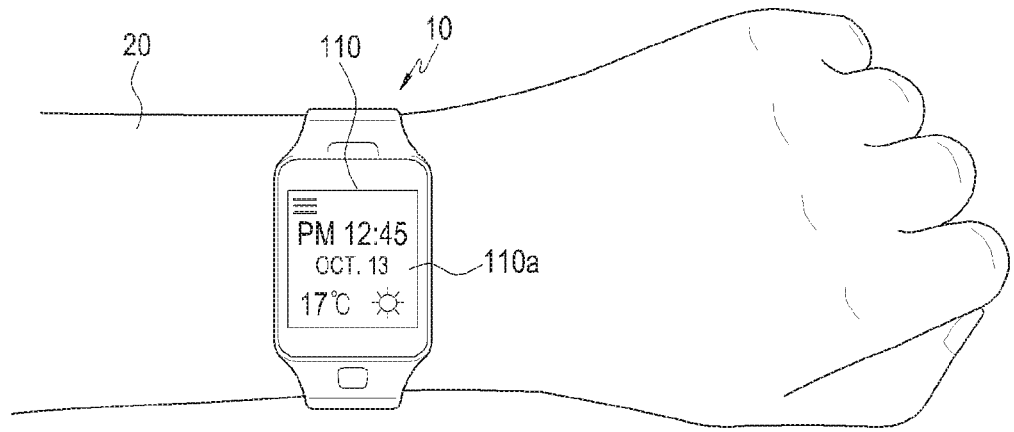
FIGS. 9A through 9D are exemplary diagrams for describing a function/operation of providing related information to a user if obtained biometric information of the user exceeds a preset threshold value according to various embodiments of the present disclosure.

Referring to FIG. 9A, when the wearable device 10 is worn on a body part of the user 20, the home screen 110a is displayed on the display unit 110.

Figure 9B:
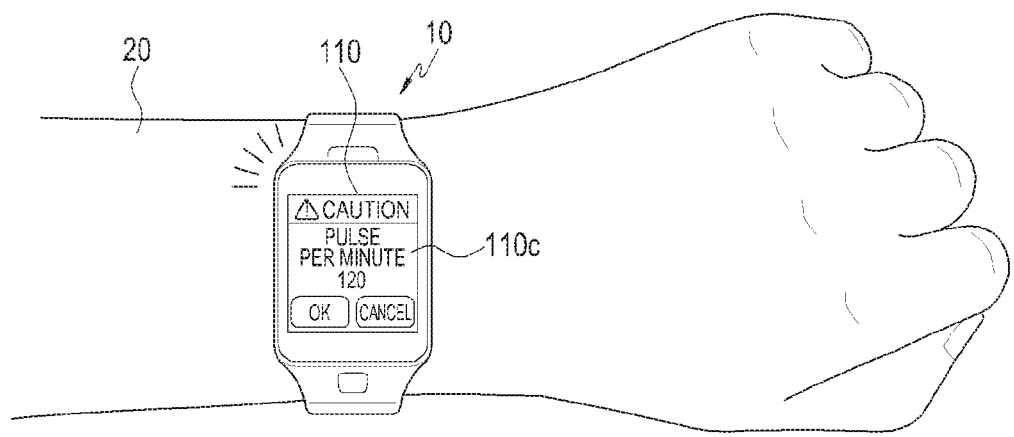

Referring to FIG. 9B, if a current pulse rate exceeds a preset threshold value (e.g., 115 pulses per minute), perhaps due to a rapid change in the biometric information, then the controller 100 notifies the user 20 that the current pulse rate exceeds the preset threshold value. The notification may be provided to the user 20 using at least one of a visual method (e.g., a color change of the screen), an audible method (e.g., a preset sound), and a tactile method (e.g., vibration).

Figure 9C:
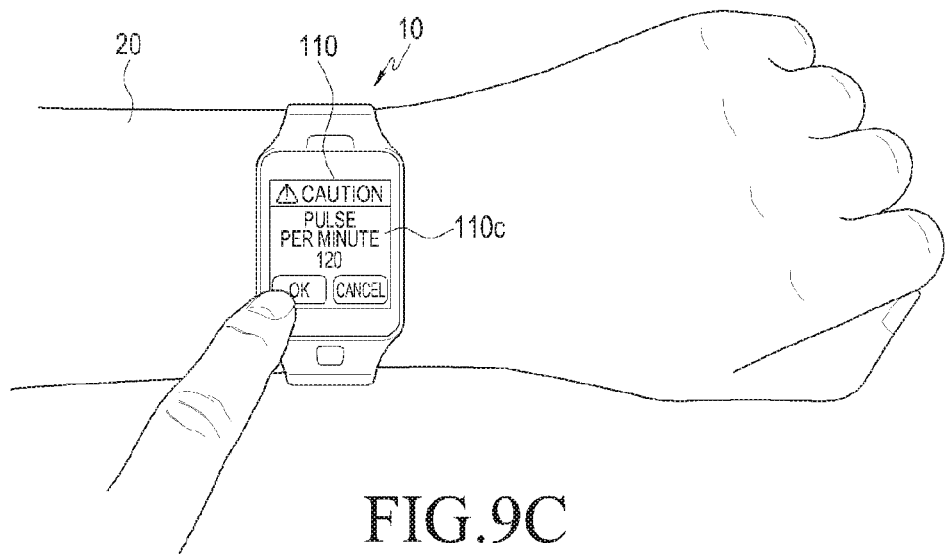
Figure 9D:
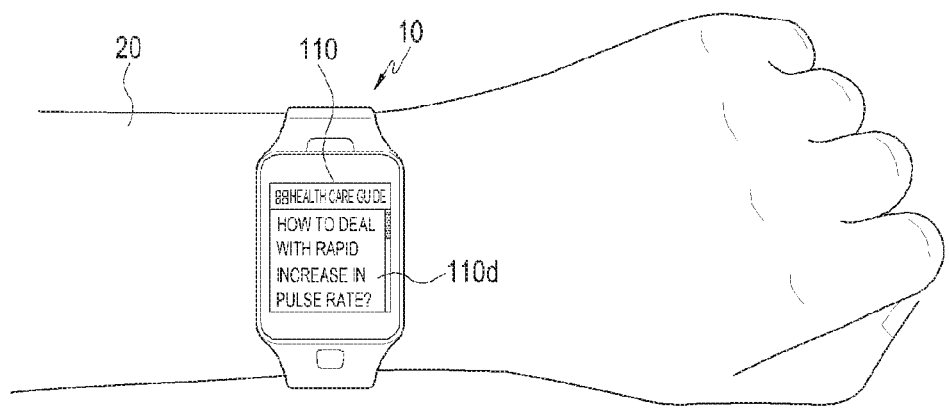

Referring to FIG. 9C, the wearable device 10 receives a request from the user 20 to check for information related to the abnormality of the biometric information (e.g., a sharp change in the pulse rate per minute). The controller 100 provides the information to the user 20 in response to the request, as illustrated in FIG. 9D. The information related to the abnormality of the biometric information may have been stored in the storage unit 150 or may be provided from another electronic device through the communication unit 130 on a real time basis.

Figure 10A:
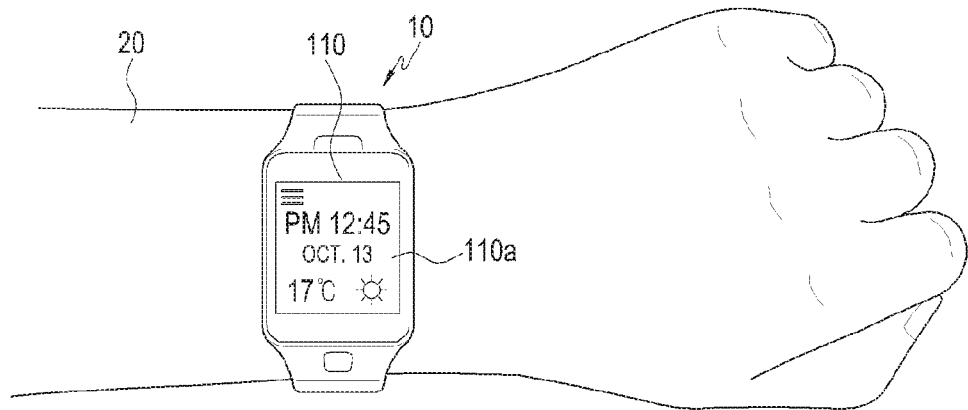
FIGS. 10A through 10C are exemplary diagrams for describing a function/operation of providing a user's history of biometric information to the user according to various embodiments of the present disclosure.
Figure 10B:
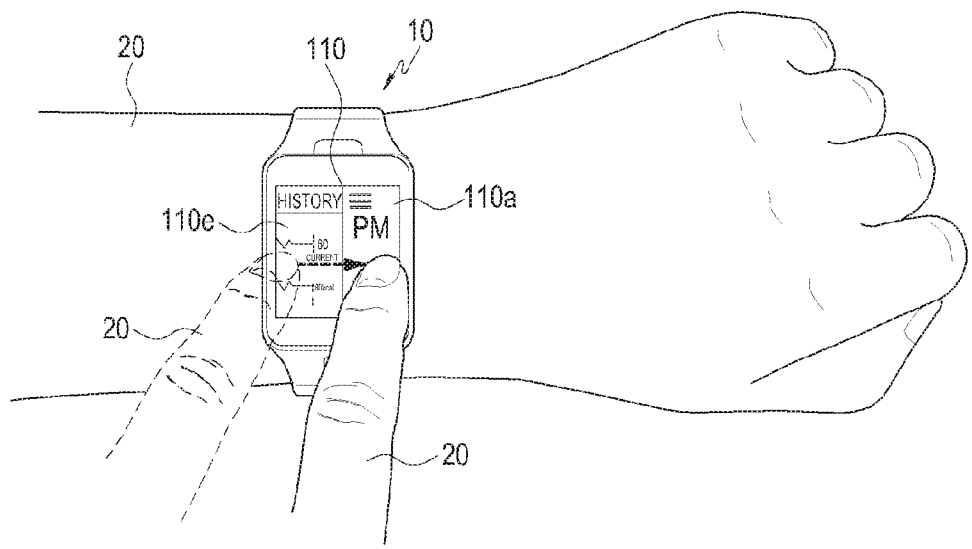
Figure 10C:
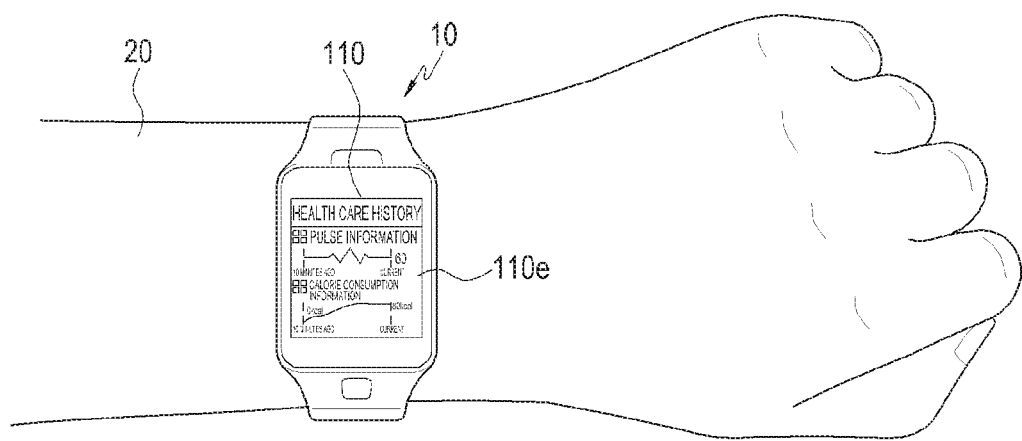

FIGS. 10A through 10C are exemplary diagrams for describing a function/operation of providing history information of biometric information of a user to the user according to various embodiments of the present disclosure.

Referring to FIG. 10A, when the wearable device 10 is worn by the user 20, the home screen 110a is displayed on the display unit 110.

Referring to FIG. 10B, with the home screen 110a is displayed on the display unit 110, the wearable device 10 may receive a drag input with respect to the home screen 110a as a screen switchover request for displaying a biometric information history screen 110e for the user 20. The drag input is an example for a description of the present disclosure, and various other input gestures may be used for screen switchover Referring to FIG. 10C, the controller 100 controls the biometric information history screen 110e to provide a history of biometric information of the user 20 obtained in a preset time range. The biometric information may be displayed on the display unit 110 in response to the screen switchover request. In FIG. 10C, a pulse rate and the amount of consumed calories are shown as examples of the biometric information.

FIGS. 11A through 11D are exemplary diagrams for describing a function/operation of providing a user with various information via an external electronic device (e.g., a smart phone) connected with a wearable device based on changes in the user's biometric information according to various embodiments of the present disclosure.

Figure 11A:
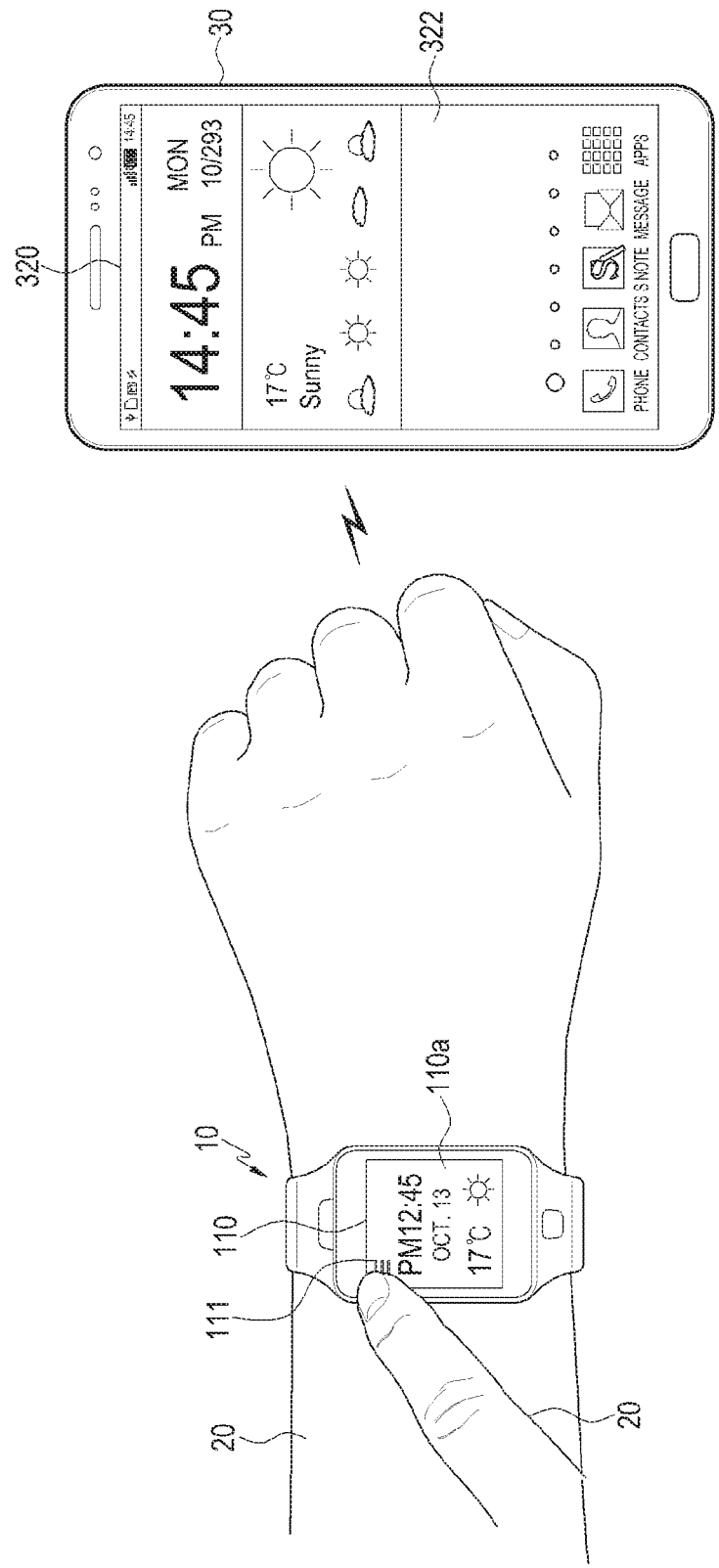
FIGS. 11A through 11D are exemplary diagrams for describing a function/operation of providing a user with various information via an external electronic device (e.g., a smart phone) connected with a wearable device based on changes in the user's biometric information according to various embodiments of the present disclosure.

Referring to FIG. 11A, the wearable device 10 is connected with another electronic device 30 through wired or wireless communication. The electronic device 30 may include a display unit 320 on which a screen 322 may be displayed. The wearable device 10 may receive an input for selecting a menu icon 111 when the home screen 110a is displayed on the display unit 110.

Figure 11B:
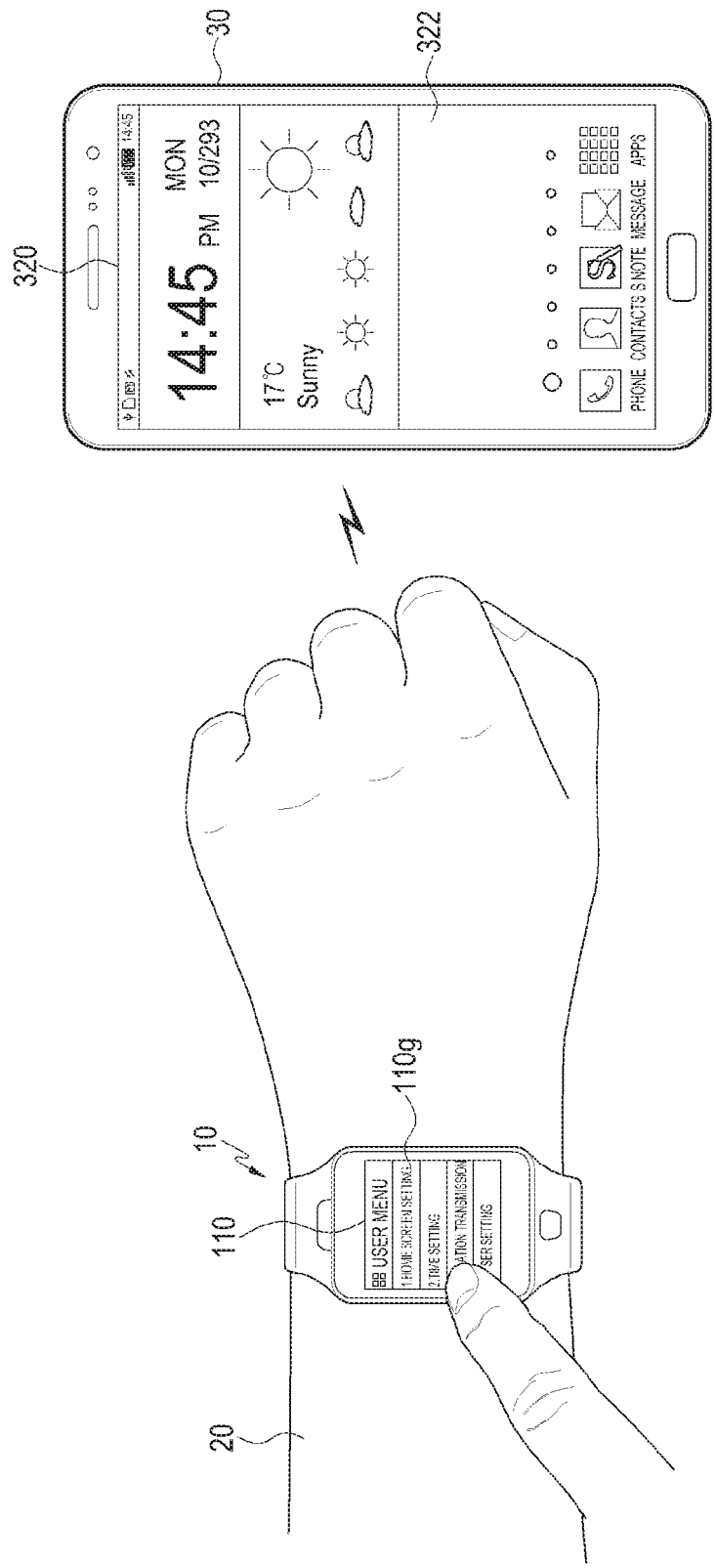

Referring to FIG. 11B, in response to the input for selecting the menu icon 111, the controller 100 controls a menu screen 110g to be displayed. The wearable device 10 receives a request for transmitting the biometric information of the user 20 stored in the storage unit 150 to the electronic device 30 from the user 20 as illustrated in FIG. 11B.

Figure 11C:
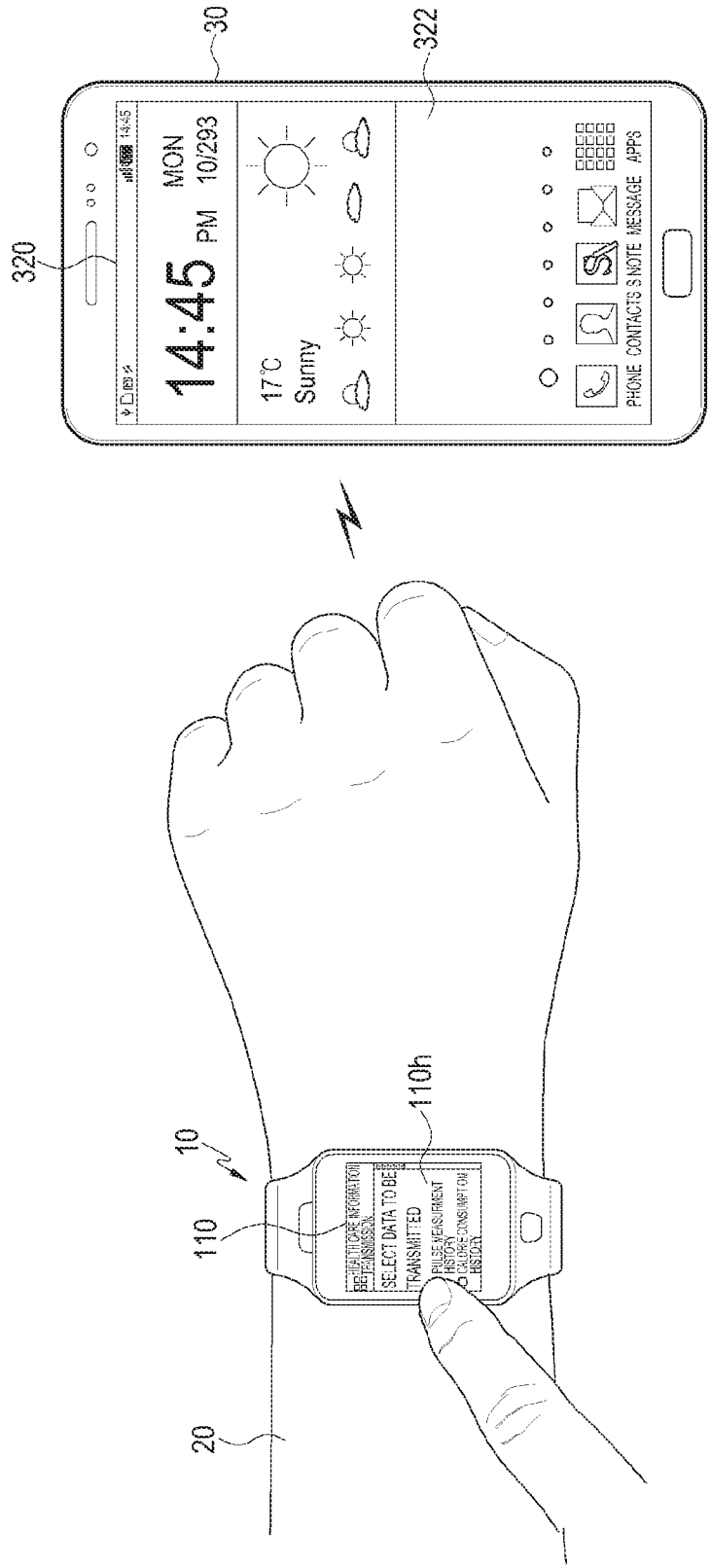

Referring to FIG. 11C, the wearable device 10 receives an input for selecting information to be transmitted to the electronic device 30 from the user 20. In FIG. 11C, as an example of the information to be transmitted to the electronic device 30, information about a pulse rate is selected.

Figure 11D:
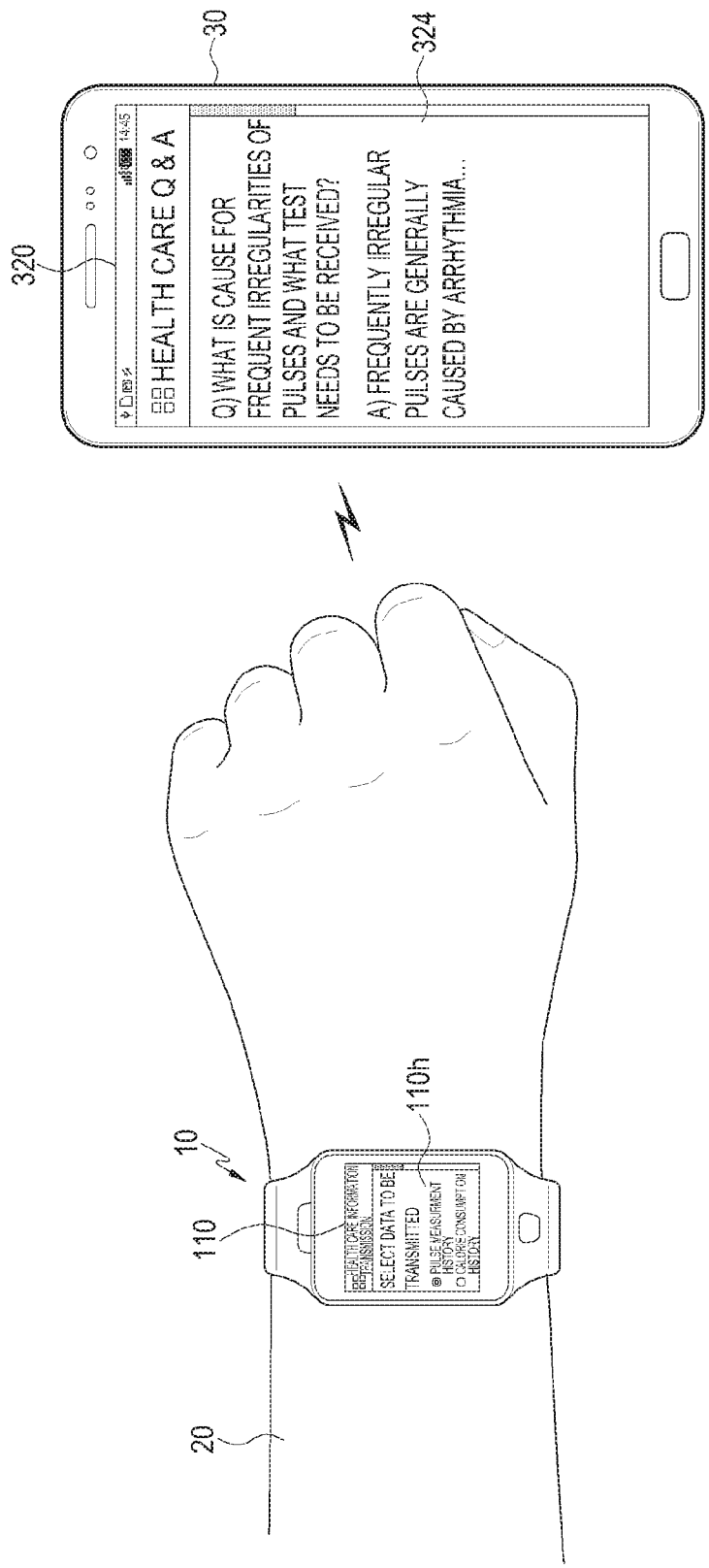

Referring to FIG. 11D, once the wearable device 10 transmits the selected biometric information to the electronic device 30, the electronic device 30 provides information related to a history of biometric information transmitted from the wearable device 10 to the user 20 through the electronic device 30. FIG. 11D shows an example of receiving information about the user 20 whose pulse rate frequently changes where a screen 324 displays information related to the frequent change of the pulse rate.

The term "unit" used in various embodiments of the present disclosure may include hardware, software, firmware, or a combination of one or more of them. The "unit" may be interchangeably used with a logic block, a component, a circuit, or the like. The "unit" may be mechanically or electronically implemented. For example, the "unit" according to various embodiments of the present disclosure may include at least one of an application-specific integrated circuit (ASIC) chip, field-programmable gate arrays (FPGAs), or programmable logic devices that perform certain operations, and other devices that may be developed.

As is apparent from the foregoing description, according to various embodiments of the present disclosure, when the user's biometric information is obtained, a movement of the wearable device due to user's motion is taken into account, thereby providing accurate biometric information to the user.

Moreover, according to various embodiments of the present disclosure, when the user's biometric information is obtained, the user's body condition is also considered to provide accurate biometric information to the user.

The effects described in the various embodiments of the present disclosure are not limited to the mentioned effects, and it will be obvious to those of ordinary skill in the art that various effects are implied herein.

The embodiments disclosed herein have been provided for description and understanding of disclosed technical matters, and are not intended to limit the scope of the present disclosure. Therefore, it should be construed that the scope of the present disclosure includes any change or other various embodiments based on the technical spirit of the present disclosure.

What is claimed is:

1. A wearable device comprising:
   a distance sensor unit configured to output a first signal for determining a distance between a user and the wearable device and to receive the first signal reflected from the user, when the wearable device is worn by the user;
   a biometric sensor unit configured to output a second signal for determining biometric information of the user for at least a portion of a position where the wearable device is worn by the user and to receive the second signal reflected from the user; and a controller configured to determine the distance based on the reflected first signal and to obtain the biometric information of the user based on a change in an attribute of the reflected second signal, wherein the controller controls the biometric sensor unit to output the second signal to the at least a portion of the position until a skin temperature of the user is increased to a reference temperature if the determined distance is equal to or less than a reference distance.

2. The wearable device of claim 1, wherein the distance sensor unit comprises a time of flight (ToF) light source configured to output the first signal and a light-receiving unit configured to receive the reflected first signal.

3. The wearable device of claim 2, wherein the controller is configured to control the ToF light source to output a wearing sensing signal for determining whether the wearable device is worn by the user at preset time intervals.

4. The wearable device of claim 1, wherein the biometric sensor unit comprises a pulse measuring light source configured to output the second signal and a light-receiving unit configured to receive the reflected second signal.

5. The wearable device of claim 1, wherein the reference distance comprises the determined distance between the user and the wearable device at an initial point in time when the wearable device is worn by the user.

6. The wearable device of claim 1, wherein the biometric information comprises at least one of pulse rate, oxygen saturation, and amount of consumed calories, and
wherein the controller is configured to control storing of the biometric information obtained during a preset time in a storage unit.

7. The wearable device of claim 6, further comprising a communication unit configured to transmit the biometric information stored in the storage unit to an electronic device connected with the wearable device through wired or wireless communication.

8. The wearable device of claim 1, wherein the controller is configured to display additional information regarding changes to specific biometric information, if the specific biometric information is above a high threshold when a normal reading of the specific biometric information is below the high threshold, or if the specific biometric information is below a low threshold when a normal reading of the specific biometric information is below the low threshold.

9. The wearable device of claim 1, further comprising a temperature sensor unit configured to sense a skin temperature of the user when the wearable device is worn by the user.

10. The wearable device of claim 9, wherein the controller controls the distance sensor unit to output the first signal during a preset time to increase the skin temperature, if the sensed skin temperature is equal to or less than a reference temperature.

11. A wearable device comprising:
a heat providing unit;
a temperature sensor unit configured to receive biometric information of a user to sense a skin temperature of the user when the wearable device is worn by the user; and
a controller configured to:
determine the skin temperature of the user for at least a portion of a position where the wearable device is worn by the user based on the biometric information received by the temperature sensor unit,
determine whether the determined skin temperature is less than a reference temperature, and
if the skin temperature of the user is less than the reference temperature, control the heat providing unit to output light to the at least a portion of the position until the skin temperature of the user is increased to the reference temperature.

12. The wearable device of claim 11, wherein the heat providing unit comprises a time of flight (ToF) light source configured to output infrared (IR) light.

13. A method for controlling a wearable device, the method comprising:
outputting a first signal for determining a distance between a user and the wearable device and receiving the first signal reflected from the user, when the wearable device is worn by the user;
determining the distance based on the reflected first signal;
outputting a second signal for determining biometric information of the user for at least a portion of a position where the wearable device is worn by the user and receiving the second signal reflected from the user, if the determined distance is equal to or less than a reference distance;
obtaining the biometric information of the user based on a change in an attribute of the reflected second signal; and
outputting the second signal to the at least a portion of the position until a skin temperature of the user is increased to a reference temperature if the determined distance is equal to or less than the reference distance.

14. The method of claim 13, wherein the first signal is output from a time of flight (ToF) light source, and the reflected first signal is received through a light-receiving unit.

15. The method of claim 14, further comprising outputting, by the ToF light source, a wearing sensing signal for determining whether the wearable device is worn by the user, at preset time intervals.

16. The method of claim 13, wherein the second signal is output from a pulse measuring light source, and the reflected second signal is received through a light-receiving unit.

17. The method of claim 13, wherein the reference distance comprises the distance between the user and the wearable device at an initial point in time when the wearable device is worn by the user.

18. The method of claim 13, wherein the biometric information comprises at least one of pulse rate, oxygen saturation, and amount of consumed calories, and the method further comprise storing the biometric information obtained during a preset time in a storage unit.

19. The method of claim 18, further comprising providing additional information regarding changes to specific biometric information, if the specific biometric information is above a high threshold when a normal reading of the specific biometric information is below the high threshold, or if the specific biometric information is below a low threshold when a normal reading of the specific biometric information is below the low threshold.

20. The method of claim 19, further comprising transmitting the biometric information stored in the storage unit to an electronic device connected with the wearable device through wired or wireless communication.

21. The method of claim 13, further comprising sensing a skin temperature of the user when the wearable device is worn by the user.

22. The method of claim 21, further comprising outputting the first signal during a preset time to increase the skin temperature, if the sensed skin temperature is equal to or less than the reference temperature.

23. A method for controlling a wearable device, the method comprising:
- receiving by a temperature sensor unit biometric information for a skin temperature of a user when the wearable device is worn by the user;
- determining the skin temperature of the user for at least a portion of a position where the wearable device is worn by the user based on the biometric information received by the temperature sensor unit;
- determining whether the determined skin temperature is equal to or less than a reference temperature; and
- if the determined skin temperature is equal to or less than the reference temperature, outputting light to the at least a portion of the position until the skin temperature of the user is increased to the reference temperature.

24. The method of claim 23, wherein the light is infrared (IR) light output from a time of flight (ToF) light source.

25. A wearable device comprising:
- a first light source unit comprising a first time of flight (ToF) light source configured to output a first signal for determining a distance between a user and the wearable device when the wearable device is worn by the user;
- a second light source unit comprising a second ToF light source configured to output the first signal and a light source configured to output a second signal for sensing a pulse of the user;
- a light-receiving unit configured to receive the first signal and the second signal reflected from the user; and
- a controller configured to determine the distance based on the reflected first signal and to obtain biometric information of the user for at least a portion of a position where the wearable device is worn by the user based on a change in an attribute of the reflected second signal,
- wherein the controller controls the light source to output the second signal to the at least a portion of the position until a skin temperature of the user is increased to a reference temperature if the determined distance is equal to or less than a reference distance.

26. A wearable device comprising:
- a controller;
- a temperature sensor unit configured to sense a skin temperature of a user wearing the wearable device;
- a first light source unit comprising a first time of flight (ToF) light source configured to output a first signal for increasing the skin temperature; and
- a second light source unit comprising a second ToF light source configured to output the first signal and a light source configured to output a second signal for obtaining biometric information of the user for at least a portion of a position where the wearable device is worn by the user,
- wherein, if the sensed skin temperature is equal to or less than a reference temperature, the controller controls the ToF light source to output the first signal to the at least a portion of the position until the skin temperature of the user is increased to a reference temperature.

* * * * *